United States Patent
Clark et al.

(10) Patent No.: US 9,693,853 B2
(45) Date of Patent: Jul. 4, 2017

(54) LUNG ELASTICITY RESTORING DEVICE AND RELATED METHODS OF USE AND MANUFACTURE

(71) Applicant: Boston Scientific Scimed Inc., Maple Grove, MN (US)

(72) Inventors: Bryan Allen Clark, Forest Lake, MN (US); Brian L. Schmidt, White Bear Lake, MN (US); Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 188 days.

(21) Appl. No.: 14/620,758

(22) Filed: Feb. 12, 2015

(65) Prior Publication Data
US 2015/0223922 A1 Aug. 13, 2015

Related U.S. Application Data

(60) Provisional application No. 61/938,911, filed on Feb. 12, 2014.

(51) Int. Cl.
*A61F 2/04* (2013.01)
*A61F 2/852* (2013.01)
*A61F 2/94* (2013.01)

(52) U.S. Cl.
CPC .............. *A61F 2/04* (2013.01); *A61F 2/852* (2013.01); *A61F 2/94* (2013.01); *A61F 2002/043* (2013.01); *A61F 2002/046* (2013.01); *A61F 2210/0014* (2013.01); *A61F 2220/0008* (2013.01); *A61F 2220/0075* (2013.01)

(58) Field of Classification Search
None
See application file for complete search history.

(56) References Cited

U.S. PATENT DOCUMENTS

| | | |
|---|---|---|
| 6,174,323 B1 | 1/2001 | Biggs et al. |
| 6,514,290 B1 | 2/2003 | Loomas |
| 6,599,311 B1 | 7/2003 | Biggs et al. |
| 6,997,189 B2 | 2/2006 | Biggs et al. |
| 8,142,455 B2 | 3/2012 | Thompson et al. |
| 8,157,823 B2 | 4/2012 | Aronson et al. |

(Continued)

FOREIGN PATENT DOCUMENTS

WO   WO 2008/027293 A2   3/2008

*Primary Examiner* — Katrina Stransky
*Assistant Examiner* — Wade P Schutte
(74) *Attorney, Agent, or Firm* — Bookoff McAndrews, PLLC

(57) ABSTRACT

A lung device for restoring lung elasticity includes fixation members and a connecting member. The fixation member includes a first radially expandable fixation member and a second radially expandable fixation member. The first radially expandable fixation member defines a first profile in an expanded state and a lumen. The second radially expandable fixation member defines a second profile in an expanded state and a lumen. The connecting member extends between and connects the first and second fixation members. The lung elasticity restoring device is capable of reversibly extendable between an inspiration configuration and an expiration configuration, may be extendable to the inspiration configuration, and biased to the expiration configuration by the connecting member.

17 Claims, 14 Drawing Sheets

(56) References Cited

U.S. PATENT DOCUMENTS

| | | |
|---|---|---|
| 8,157,837 B2 | 4/2012 | Thompson et al. |
| 8,282,660 B2 | 10/2012 | Thompson et al. |
| 8,574,284 B2 * | 11/2013 | Roeder ................... A61F 2/07 623/1.13 |
| 2005/0119729 A1 * | 6/2005 | Coppi ...................... A61F 2/06 623/1.27 |
| 2006/0200191 A1 * | 9/2006 | Zadno-Azizi .... A61B 17/12045 606/200 |
| 2008/0065205 A1 * | 3/2008 | Nguyen ................ A61F 2/2451 623/2.36 |
| 2009/0088836 A1 * | 4/2009 | Bishop ................ A61F 2/2418 623/2.1 |
| 2010/0305715 A1 | 12/2010 | Mathis et al. |

* cited by examiner

LUNG ELASTICITY RESTORING DEVICE AND RELATED METHODS OF USE AND MANUFACTURE

CROSS-REFERENCE TO RELATED APPLICATIONS

The present application claims the benefit of U.S. Provisional Application 61/938,911, filed Feb. 12, 2014.

TECHNICAL FIELD

The present disclosure pertains to medical devices, and methods for using and manufacturing medical devices. More particularly, the present disclosure pertains to medical devices that can restore elasticity of lungs.

BACKGROUND

Chronic obstructive pulmonary disorder (COPD), also known as chronic obstructive lung disease, is a progressive disorder of lungs that affects breathing efficiency and capacity of lungs. COPD involves the occurrence of chronic bronchitis and emphysema, in which the ability of the lungs to exhale air completely is reduced. This condition leads to a loss of elasticity in the lungs, thereby leading to reduced or minimal gas exchange, air trapping, and/or hyperinflation of lungs. Other factors that may affect lung performance include airway inflammation, mucus hyper secretion, and airway hyper responsiveness. Also, the lungs may get hyper expanded when excessive air is trapped in the lungs. The hyper expanded lung tissue causes inefficient breathing and further deteriorates the lung's condition.

Certain medical techniques to treat COPD may include lung volume reduction surgery (LVRS). This technique involves a surgical resection of a diseased portion of the lungs, thereby allowing the remaining undiseased or unchallenged portion of the lungs to function normally. This technique is ideal for the upper lobes of the lungs. However, this technique has associated post-operative risks, such as bleeding, extensive damage to lungs, and sometimes death of the patient, etc. Other less invasive techniques for treating the diseased lungs/COPD include endobronchial valves, reduction coils, heated water vapor, polymeric injection, etc. Challenges associated with endobronchial valves include blockage of the non-diseased portion of the lung, leading to further inefficient breathing.

It may therefore be beneficial to treat lung conditions that affect elasticity, such as COPD, while at the same time reducing, minimizing or avoiding the above and/or other risks.

SUMMARY

One embodiment is a lung device configured to be deployed in an airway. The lung device includes fixation members and a connecting member. The fixation members include a first radially expandable fixation member and a second radially expandable fixation member. The first radially expandable fixation member has a first profile in an expanded state and defines a lumen. The second radially expandable fixation member has a second profile in an expanded state and defines a lumen. The connecting member extends between and connects the first and second fixation members. The connecting member is elastic or super elastic such that the connecting member has a rest state and a stretched state. The lung device is capable of being reversibly extendable between an inspiration configuration and an expiration configuration, and in particular, the lung device is extendable to the inspiration configuration and biased to the expiration configuration by the connecting member so as to aid in restoring elasticity to the lung or lungs where the device is deployed.

Another embodiment includes a lung elasticity restoring device that includes a first stent having a first profile in an expanded state. The lung elasticity restoring device also includes a second stent having a second profile in an expanded state. The first stent forms a first end and the second stent forms a second end of the lung elasticity restoring device. The lung elasticity restoring device further includes a connecting member extending between and connecting the first and second stents. The connecting member is elastic or super elastic such that the connecting member has a rest state and a stretched state. The lung elasticity restoring device is capable of being reversibly extendable between an inspiration state and an expiration state, and is expanded to the inspiration state and biased to the expiration state by the connecting member. The connecting member remains in the rest state while the lung elasticity restoring device is in the expiration state, and the connecting member assumes the stretched state when the lung elasticity restoring device is in the inspiration state.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

A detailed description of the present disclosure is hereafter described with specific reference being made to the drawings.

Figure 1A:
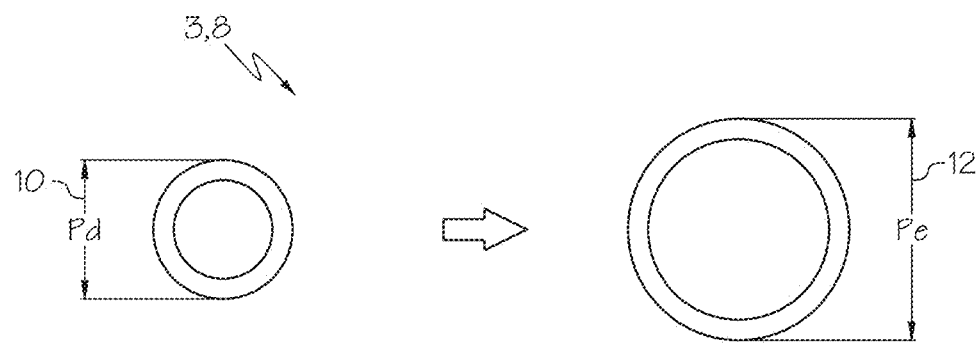
FIGS. 1A-1C are cross-sectional views of exemplary stent fixation members in a delivery state and an expanded state.

While the disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the disclosure.

DETAILED DESCRIPTION

Definitions are provided for the following defined terms. It is intended that these definitions be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

References in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure, or characteristic is described in connection with one embodiment, it should be understood that such feature, structure, or characteristic may also be used in connection with other embodiments, whether or not explicitly described unless clearly stated to the contrary.

As used herein "diameter" is the distance of a straight line extending between two points and does not indicate a particular shape.

The following detailed description should be read with reference to the drawings in which similar elements in different drawings are numbered the same. The drawings, which are not necessarily to scale, depict illustrative embodiments and are not intended to limit the scope of the disclosure.

Some embodiments of the present disclosure are directed to deploying a lung elasticity restoring device 2 in a lung 900 to reduce lung hyperinflation. The lung elasticity restoring device 2 is configured to 1) maintain the airways in an open state; 2) provide elastic recoil properties to help expel air from the airways during exhalation; 3) reduce, minimize or prevent over-expansion of a portion of the lung 900; and combinations thereof. In some embodiments, the lung elasticity restoring device 2 includes at least one fixation member 3 and at least one connecting member 4. In other embodiments, the lung elasticity restoring device 2 includes at least one fixation member 3, at least one connecting member 4, and a respiration assistance member 5. The lung elasticity restoring device 2 may further include a valve 46.

Figure 12:
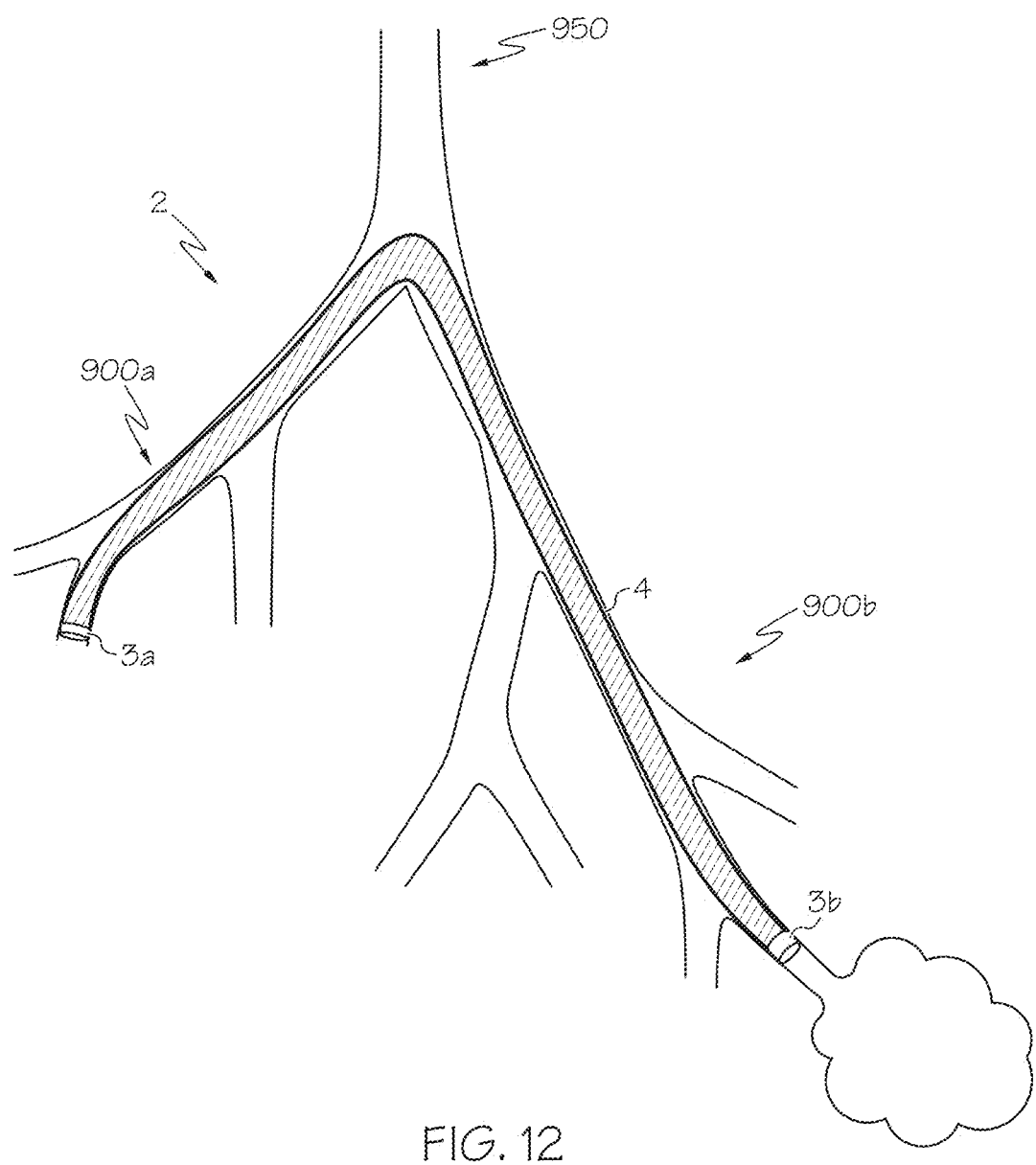
FIG. 12 is a view of an exemplary lung elasticity restoring device implanted in a lung.
Figure 13:
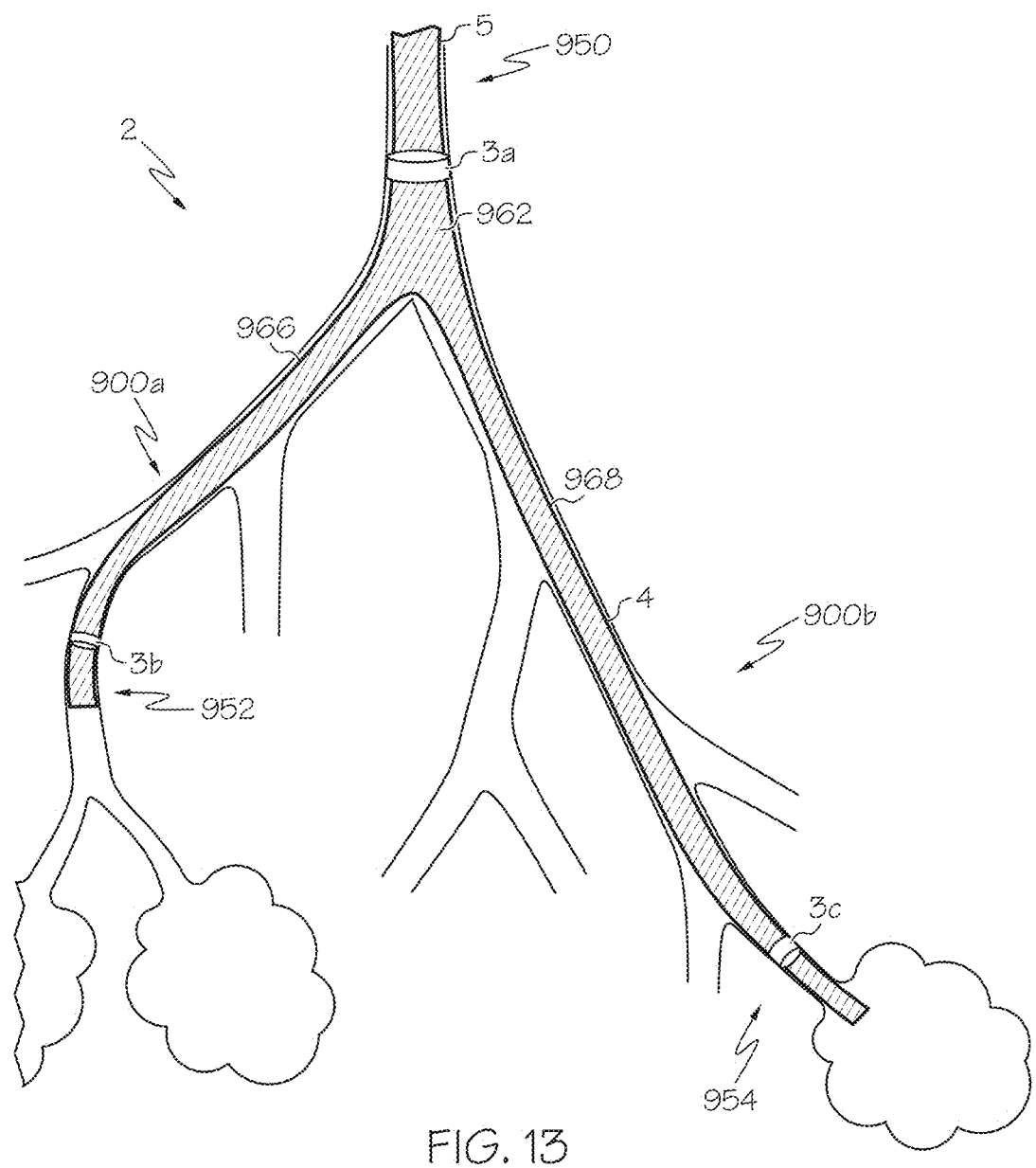
FIG. 13 is a view of an exemplary bifurcated lung elasticity restoring device implanted in a lung.
Figure 14:
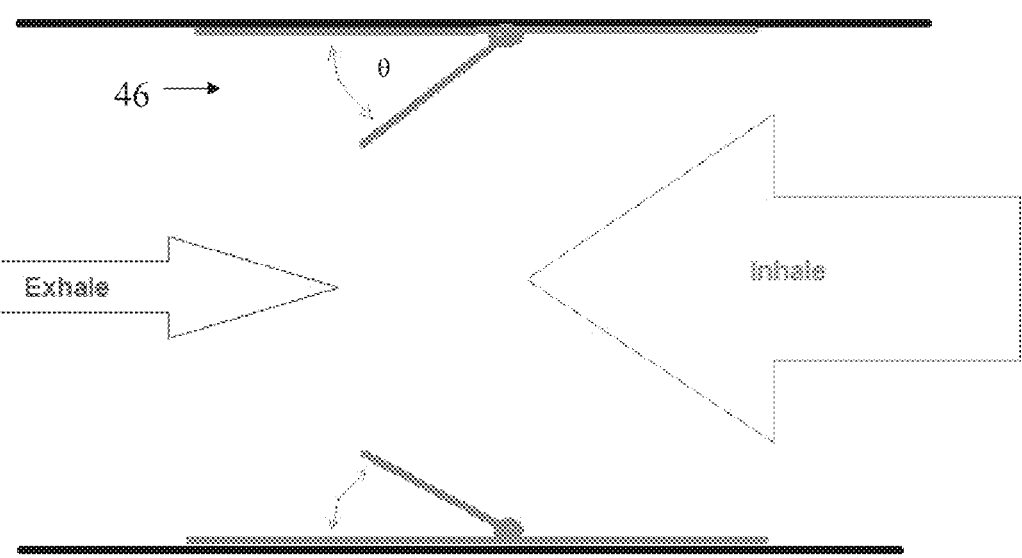
FIG. 14 is a schematic view of a valve constructed and arranged to partially close on exhalation.

FIGS. 1A-1C, 2A-2B, 3 and 4 depict different embodiments of the fixation member 3; FIGS. 5A-5F, 6, 7, and 8 depict different embodiments of the connecting member 4; FIG. 14 shows a schematic cross-sectional view of a valve 46; and FIGS. 9A-E, 10, 11A-1B, 12, and 13 depict different configurations of the lung elasticity restoring device 2, and different implantation configurations in one or both lungs. Fixation members 3, connecting members 4, the respiration assistance member 5, and the lung elasticity restoring device 2, are discussed in greater detail below.

A. Fixation Members

Figure 11A:
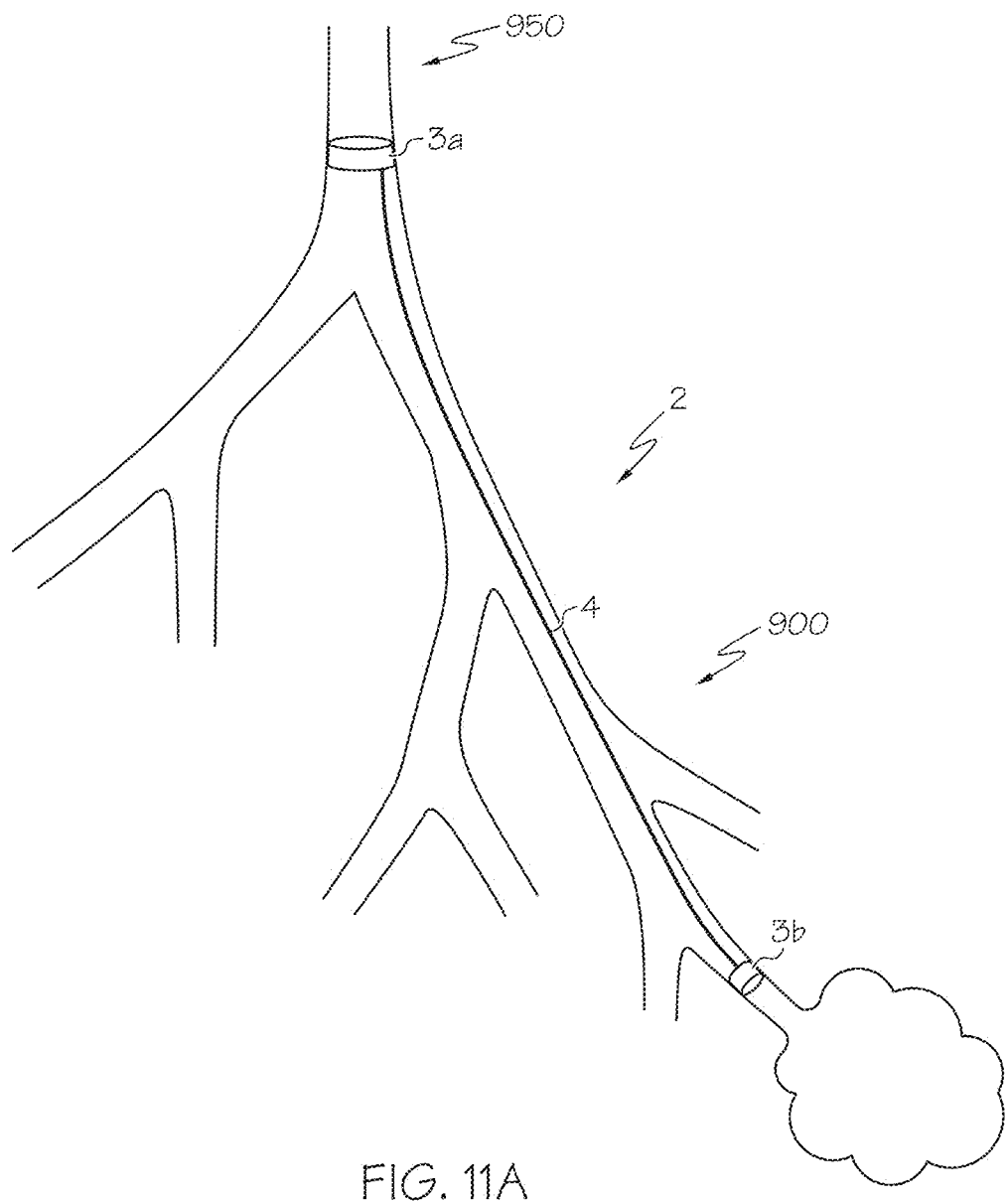
FIGS. 11A-11B are views of an exemplary lung elasticity restoring device implanted in a lung, in inspiration and expiration configurations respectively.
Figure 11B:
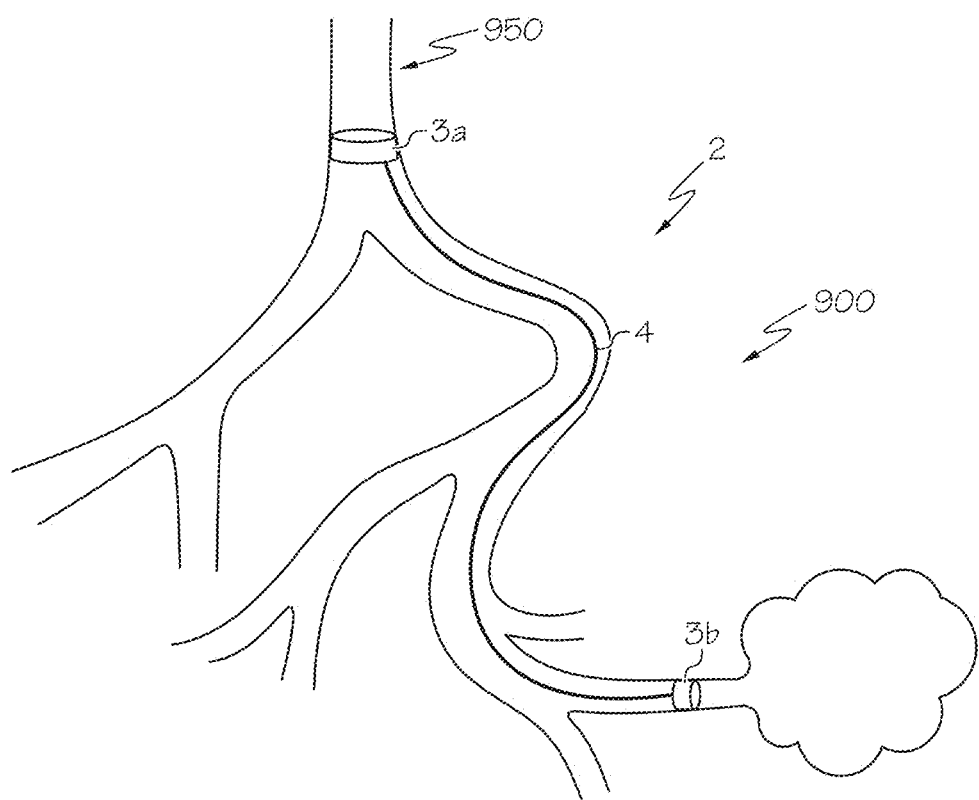

As noted above, the lung elasticity restoring device 2 has at least one fixation member 3. FIGS. 11A-B and 12 show a lung elasticity restoring device 2 with two fixation members 3a, 3b and FIG. 13 shows a lung elasticity restoring device 2 with three fixation members 3, 3b, 3c. However, the lung elasticity restoring device 2 can have four, five, six, or more fixation members 3. In at least one embodiment, the lung elasticity restoring device 2 has a fixation member 3 at each of the ends of the lung elasticity restoring device 2. The fixation members 3 of a lung elasticity restoring device 2 may be the same or may be different from one another.

In at least one embodiment, the fixation member 3 is deployed inside an airway of a diseased or otherwise challenged lung 900 along the internal circumference of the airway. As the lungs 900 inhale air, the airways of the lung 900 expand. In some embodiments, the fixation member 3 is configured to expand and contract as the airway expands during inhalation and contracts during exhalation. In other embodiments, the fixation member 3 conforms to the airway upon deployment. The fixation member 3 can have any length that enables it to perform the above operation or function and for deployment in a desired airway. In some embodiments, the fixation member 3 has a maximum length of 12 cm and a minimum length of 0.10 cm. The fixation member 3 defines a lumen.

In at least one embodiment, the fixation member 3 in the expanded state has a greater diameter or profile as compared to that in the delivery state, as represented by Pe and Pd states, respectively. Here, "the expanded state 'Pe'" refers to the state of the fixation member 3 when deployed in the airway and "the delivery state 'Pd'" refers to the state of the fixation member 3 during delivery to the lung 900, e.g., when the fixation member 3 is within a delivery tube or sheath before deployment of the fixation member 3 by radial expansion.

When implanted the fixation member 3 holds open the local region of the airway where the fixation member 3 is located. In some embodiments, the fixation member 3 has a maximum diameter or profile in the expanded state (Pe) of about 0.05 cm to about 1.80 cm for implantation in airways ranging from a respiratory bronchiole to the trachea. The fixation member 3 is configured to expand radially to a certain extent, so that the airways/lungs are not over-expanded and to minimize excessive airway trauma. In some embodiments, the fixation member 3 when implanted expands the lumen of the airway in the local region to a reasonable amount, for example, not more than 50% of the original diameter of the lumen. Also, when the fixation member 3 is implanted, air traverses through the lumen defined by the fixation member.

Suitable materials for the fixation members 3 are discussed below. In some embodiments, the fixation member 3 has a cross-sectional shape, such as but not limited to, circular, oval, elliptical, ovoid, oblong, or an irregular shape, etc., in the delivery state (Pd), in the expanded state (Pe), and/or during expansion to the expanded state (Pe). Exemplary cross-sectional shapes are discussed below in greater detail.

The fixation member 3 is either a stent fixation member 8 or a balloon fixation member 100. FIGS. 1A-C, 2A-B, and 3 show examples of stent fixation members 8 and FIG. 4 shows an example of a balloon fixation member 100. A lung elasticity restoring device 2 can include only stent fixation members 8, only balloon fixation members 100, or a combination of stent fixation and balloon fixation members 8, 100.

i. Stent Fixation Members

In some embodiments, the stent fixation member 8 is a solid piece of material. In other embodiments, the stent fixation member 8 has a plurality of openings through the wall and is not a solid piece of material.

Figure 1B:
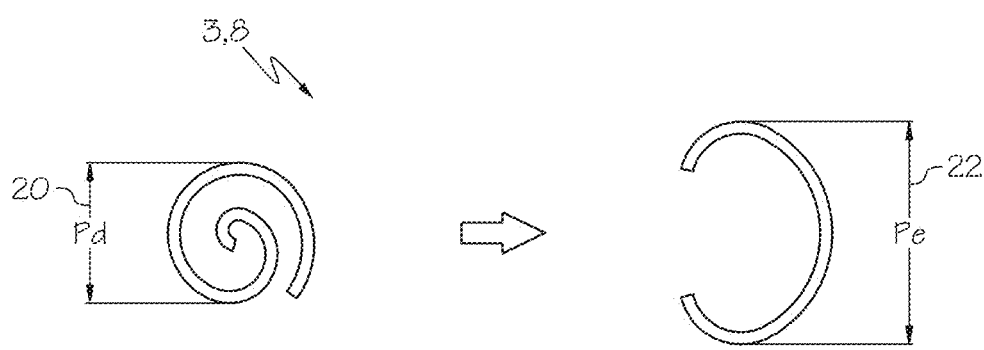

In some embodiments, the stent fixation member 8 has a circular shape in the delivery state (Pd) 10 and in the expanded state (Pe) 12, as shown for example in FIG. 1A. As can be seen, the stent fixation member 8 has larger diameter in the expanded state (Pe) 12 as compared to the diameter in the delivery state (Pd) 10. In this embodiment, the stent fixation member 8 defines a single lumen in the expanded state (Pe) 12. In other embodiments, for example as shown in FIG. 1B, the stent fixation member 8 is spiral shaped in the delivery state (Pd) 20 and is semi-tubular in the expanded state (Pe) 22. In some embodiments, the semi-tubular configuration is C-shaped in the expanded state (Pe) 22. A portion extending longitudinally along the stent fixation member 8 in the expanded state (Pe) 22 is open, thereby leaving a longitudinal portion of the airway uncovered. In at least one embodiment, a stent fixation member 8 with a semi-tubular shape in the expanded state (Pe) 22 is employed so that cilia present on the uncovered portion of the airway can perform their function of sweeping the mucus up and out of the lungs. In this embodiment, the stent fixation member 8 defines a single lumen in the expanded state (Pe) 22.

Figure 1C:
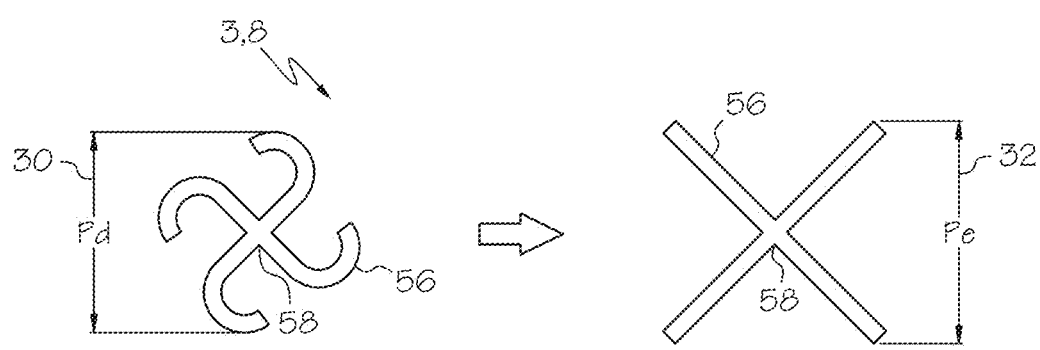

In some embodiments, the stent fixation member 8 has radial members 56 extending from a longitudinal core 58. FIG. 1C depicts another embodiment of the stent fixation member 8 that has four radial members 56. However, the stent fixation member 8 can have two, three, four, five, six or more radial members 56 extending from a longitudinal core 58. When this stent fixation member 8 embodiment is implanted in an airway, a plurality of lumens for air to flow therethrough are defined. In some embodiments, the plurality of air lumens is defined in part by the stent fixation member 8 and in part by the inner surface of the airway.

In at least one embodiment, the radial members 56 fold down for delivery and expand outwards for the expanded state (Pe) 32. In some embodiments, the radial members 56 are curved when the stent fixation member 8 is in the delivery state (Pd) 30, and straight when the stent fixation member 8 is in the expanded state (Pe) 32, as shown for example in FIG. 1C. In one embodiment, the ends of straight radial members 56 penetrate through an internal surface of the airway when the stent fixation member 8 is implanted. In another embodiment, the ends of the straight radial members 56 do not penetrate through an internal surface of the airway when the stent fixation member 8 is implanted. In other embodiments, the radial members 56 are curved when the stent fixation member 8 is in the delivery state (Pd) 30 and when the stent fixation member 8 is in the expanded state (Pe) 32. In this embodiment, the expanded state (Pe) 32 would have a similar configuration as that shown for the delivery state (Pd) 30 in FIG. 1C. In one embodiment, the curved end region of one or more radial members 56 of the stent fixation member 8 conforms to the inner surface of the airway when the stent fixation member 8 is in the expanded state (Pe) 32.

Figure 2A:
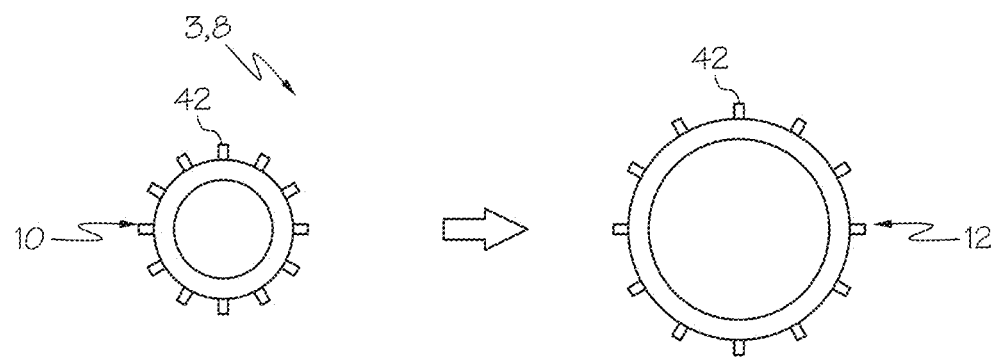
FIGS. 2A-2B are cross-sectional views of the exemplary stent fixation member of FIGS. 1A and 1B with protrusions.
Figure 2B:
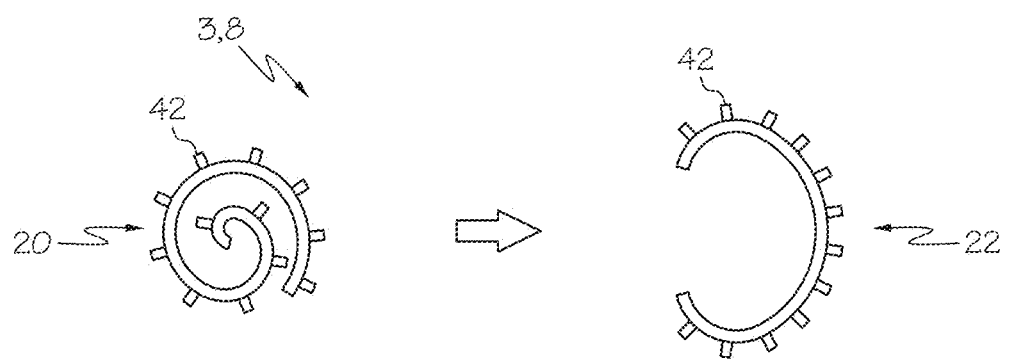

FIGS. 2A and 2B show cross-sectional views of the stent fixation member 8 of FIGS. 1A and 1B with a number of protrusions 42 positioned on an outer surface of the stent fixation member 8. FIGS. 2A and 2B respectively show the Pd states 10, 20 and the Pe states 12, 22 of the stent fixation member 8.

In some embodiments, the protrusions 42 do not penetrate an internal surface of the wall of the airways of the lungs. In this embodiment, there is a space equal to a length of the protrusions 42 between the outer surface of the stent fixation member 8 and the inner surface of the airway. In one embodiment, the space between the outer surface of the stent fixation member 8 and the inner surface of the airway provides for cilia to perform their function of sweeping mucus up and out of the lungs.

In other embodiments, the protrusions 42 penetrate an internal surface of walls of the airways of the lungs, thereby anchoring the stent fixation member 8 to the internal surface of the airway upon expansion to the Pe state 12, 22. In such instances, the protrusions 42 only penetrate to a reasonable depth so that the protrusions 42 do not harm the airway. The protrusions 42 can penetrate into the inner surface of the airway to a depth less than 5 mm. More preferably, the protrusions 42 can penetrate into the inner surface of the airway to a depth less than 2 mm. Thus, in some embodiments, the protrusions 42 penetrate into the wall of an airway for a maximum of 5 mm, and in other embodiments the protrusions 42 penetrate into the wall of an airway for a maximum of 2 mm.

Figure 3:
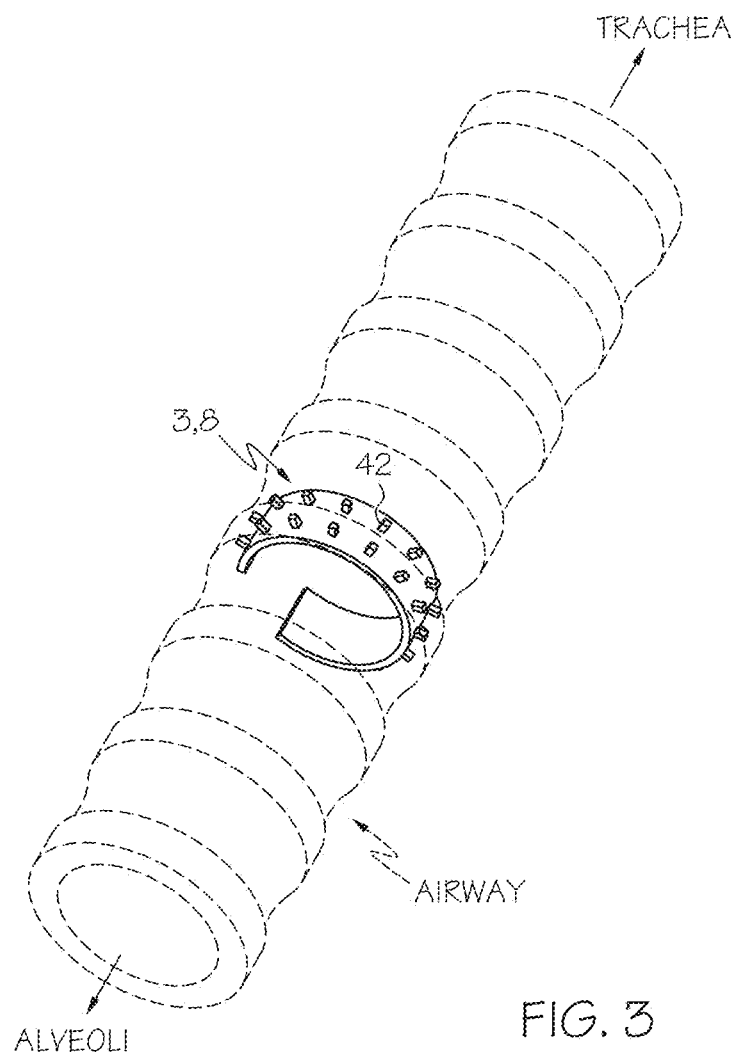
FIG. 3 is a schematic view showing the orientation of the protrusions of a stent fixation member relative to lung anatomy.
Figure 4:
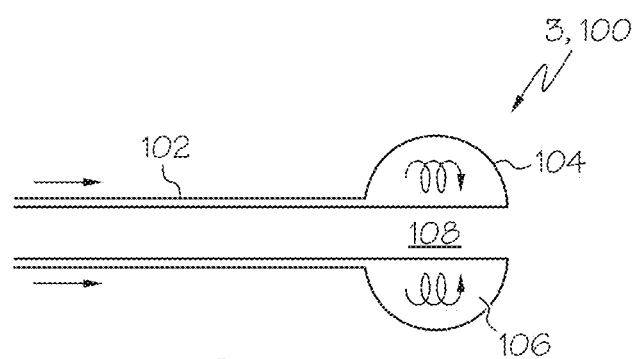
FIG. 4 is a cross-sectional view of an exemplary balloon fixation member.

FIG. 3 depicts an exemplary orientation of the protrusions 42 relative to lung anatomy. As described above, the protrusions 42 secure the stent fixation member 8 to the airway. In some embodiments, the protrusions 42 are oriented away from the alveoli and towards the trachea when the lung elasticity restoring device 2 is implanted. In other embodiments, protrusions 42 that are oriented away from the alveoli and towards the trachea help maintain the position of the lung elasticity restoring device 2 in the airway during exhalation when the lung elasticity restoring device 2 contracts to the expiration configuration. Without being bound by theory, orienting the protrusions 42 away from alveoli may increase the force required for the fixation member 8 to translate (migrate) in the direction away from alveoli. In other embodiments, the protrusions 42 are perpendicular to the outer surface of the fixation member 8.

In at least one embodiment, the stent fixation member 8 is covered or lined. The outer surface, the inner surface, or both the inner and outer surfaces of the stent fixation member 8 can be lined or covered. Suitable materials for the liner or cover are discussed below.

ii. Balloon Fixation Members

As discussed above, the fixation member 3 can be a balloon fixation member 100. The balloon fixation member 100 is an annular balloon 104 with a wall that defines an interior inflation lumen 106 and an exterior lumen 108. Suitable materials for the balloon 104 are discussed below.

In some embodiments, at an implantation site the balloon 104 is expanded a predefined amount and becomes anchored firmly with the internal walls of the airway. In this embodiment, the balloon fixation member 100 is uninflated in the delivery state (Pd) (not shown) and inflated in the expanded state (Pe). When the balloon fixation member 100 is implanted air from the airway flows through the exterior lumen 108. In some embodiments, the outer surface of the balloon 104 has texturing or small protrusions that function to anchor the balloon fixation member to an airway as described above for protrusions 42 on stent fixation members 8. In one embodiment, the texturing or small protrusions reduces the amount of airway wall in direct contact with the outer surface of the balloon fixation member 100.

In some embodiments, the balloon fixation member 100 is inflated by a detachable inflation mechanism 102, which is shown in FIG. 4. In some embodiments, the detachable inflation mechanism 102 is a hollow elongated member. In some embodiments, the detachable inflation mechanism 102 extends from the balloon fixation member 100 to a proximal end of a delivery device.

To inflate the balloon 104, inflation media is introduced into the interior inflation lumen 106 by the detachable inflation mechanism 102 which is in fluid communication with an inflation media source and the interior inflation lumen 106 of the balloon 104. In some embodiments, the detachable inflation mechanism 102 is detachably connected to the balloon 104 by an inflation valve (not shown) in the outer wall of the balloon 104. When the inflation mechanism 102 is detached from the balloon fixation member 100, the inflation valve prevents fluid from escaping the interior inflation lumen 106 of the balloon 104. In one embodiment, the detachable inflation mechanism 102 is withdrawn from the balloon fixation member 100 after the balloon 104 is inflated. In some embodiments, to withdraw the lung elasticity restoring device 2 from an implantation site, the inflation media is removed from the balloon fixation member 100 through the inflation valve in order to deflate the balloon 104.

Suitable materials for the inflation media used to expand the balloon fixation member 100 include air, a fluid that remains in a fluid state, or a fluid that solidifies over time. An example of a fluid that solidifies over time is a medical grade adhesive. Examples of fluids that remain in a fluid state include liquid silicone, and saline.

B. Connecting Members

As discussed above, the lung elasticity restoring device 2 has at least one connecting member 4 extending between and connecting (directly or indirectly) the fixation members 3 of the lung elasticity restoring device 2. As discussed below in greater detail, the connecting member 4 can be a tubular member, a band, a cord, a wire, interconnected structures, and combinations thereof.

In at least one embodiment, the connecting member 4 is connected to the fixation members 3 by methods such as welding, bonding, or the other methods that are known in the art. Bonding methods include fusion bonding or adhesive bonding. Suitable materials for the connecting members are discussed below. In some embodiments, the connecting member 4 is connected to an interior surface of the fixation member 3

Figure 9A:
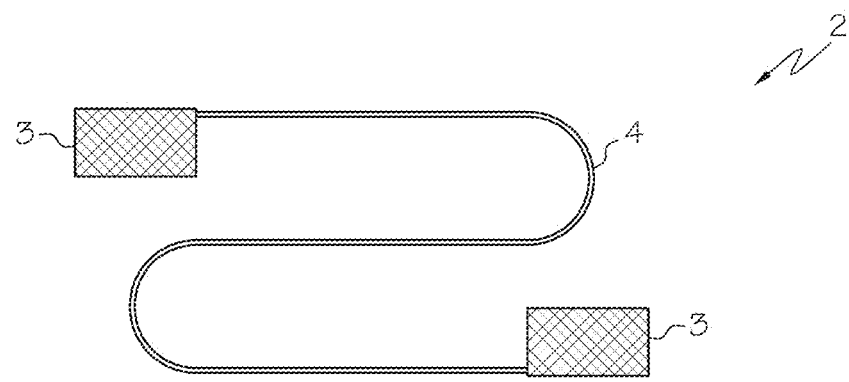
FIGS. 9A-9E are views of exemplary configurations for the free state of a connecting member.
Figure 9B:
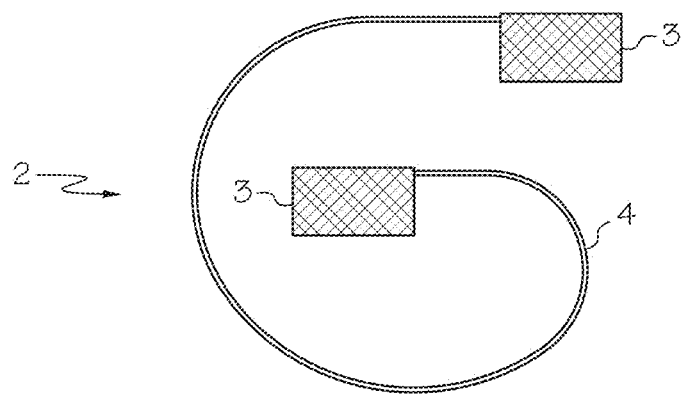
Figure 9C:
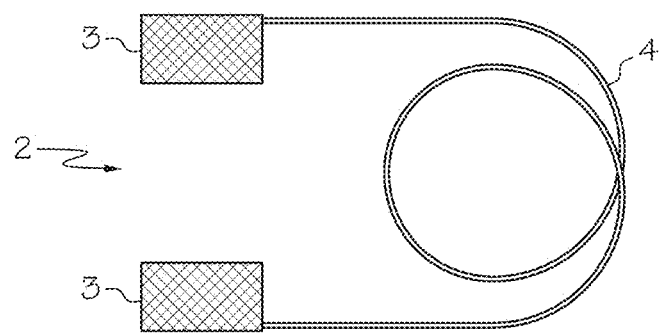
Figure 9D:
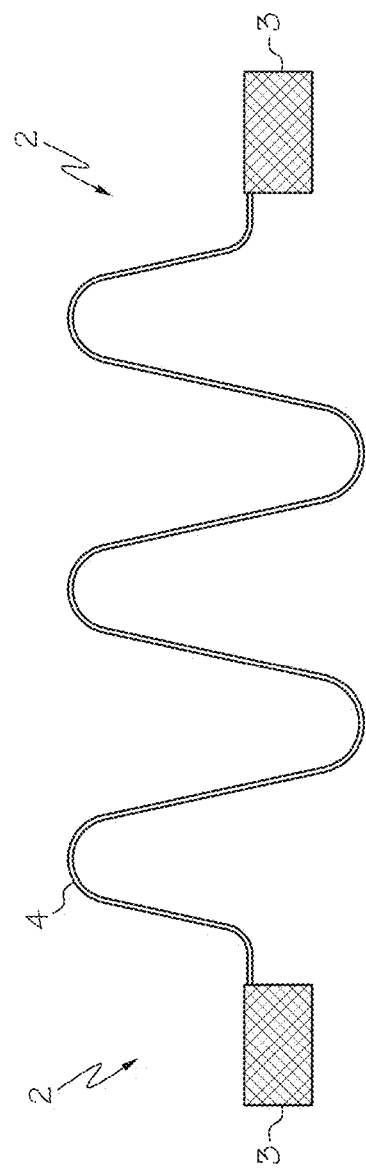
Figure 9F:
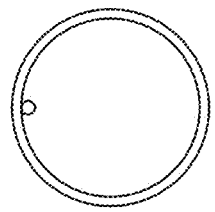
FIG. 9F is an end view of the lung elasticity restoring device of FIG. 9E.
Figure 9E:
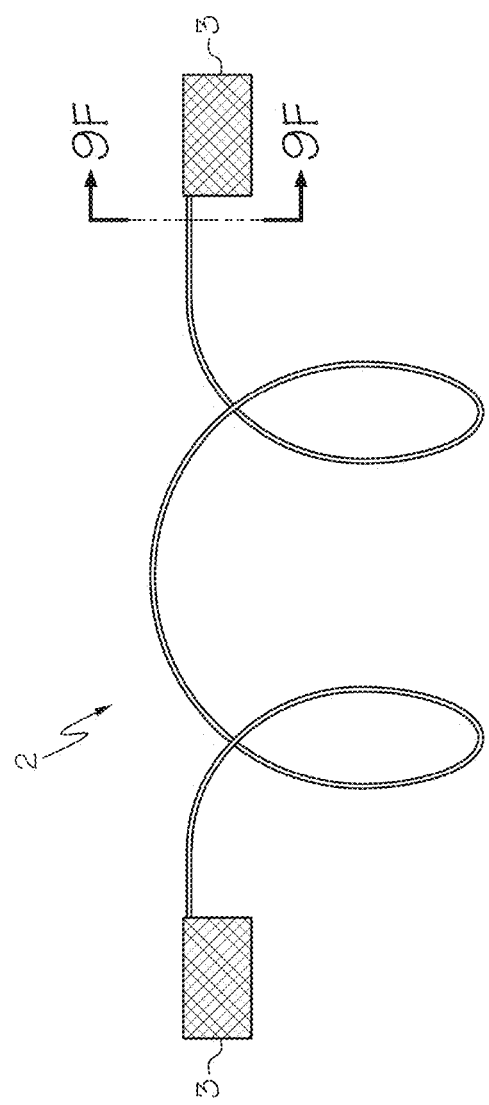

FIGS. 9A-F shows different exemplary configurations for the free state of the connecting member 4: semi-circular (FIG. 9B), spiral (FIG. 9C), sinusoidal wave (FIG. 9D), and bi-looped (FIG. 9E). Although the connecting member 4 in FIGS. 9A-F is a superelastic wire, the other connecting member 4 embodiments discussed below can have these configurations in the free state.

As used herein the "free state" of the connecting member 4 is a state of the member where no force is being applied to the connecting member 4; in other words the connecting member 4 is fully unconstrained, as for example when the lung elasticity restoring device 2 is placed on a counter. In contrast, the connecting member 4 is constrained when implanted in the airway.

In at least one embodiment, the connecting member 4 provides the lung elasticity restoring device 2 with elastic recoil properties. When implanted, the connecting member 4 has a rest state and a stretched state so that the connecting member 4 longitudinally expands from the rest state to the stretched state during inhalation and longitudinally retracts from the stretched state to the rest state during exhalation. Thus, the "rest state" can be referred to as an expiration state, and the "stretched state" can be referred to as an inspiration state. In some embodiments, the longitudinal length of the connecting member 4 changes from a rest length to a stretched length which is greater than the rest length. For example, a connecting member 4 formed of elastic material can be stretched from a rest length to a stretched length. In other embodiments, the connecting member 4 has a uniform longitudinal length but the longitudinal extent of the connecting member 4 is less in the rest state than in the stretched state.

Figure 10:
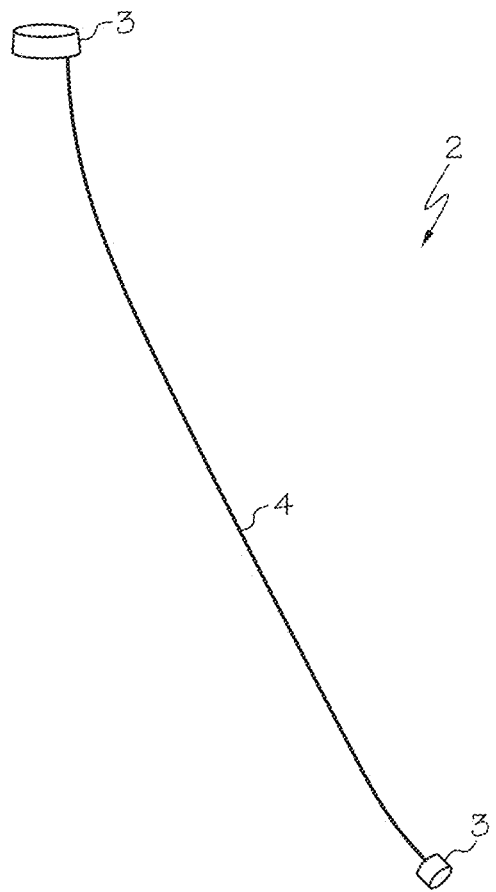
FIG. 10 is a view of an exemplary inspiration configuration of an exemplary lung elasticity restoring device.

FIG. 10 depicts an example of a lung elasticity restoring device 2 in a stretched state. Although the connecting member 4 shown in FIG. 10 is substantially straight, depending on the constraints imposed by the airways and the implantation location the connecting member 4 can include one or more bends. The configuration of the connecting member 4 in the rest state depends on the constraints imposed by the airways on the implanted lung elasticity restoring device 2. Without being bound by theory, the configuration of the connecting member 4 in the rest state is likely to be somewhat straighter than the free state and somewhat curvier than the stretched state. In at least one embodiment, the connecting member 4 in the rest state has at least one bend. In some embodiments, the connecting member 4 has a serpentine shape in the airway when in the rest state. These configurations are non-limiting as the connecting member 4 can have other configurations in its rest state and stretched state that provide the elastic recoil properties of the lung elasticity restoring device 2.

In at least one embodiment, the connecting member 4 has a maximum radial extent or diameter of 1.80 cm, and a minimum radial extent or diameter of 0.05 cm. In some embodiments, a portion of the connecting member 4 remains in direct contact with the inner surface of the wall of the airway during inhalation and exhalation when the lung elasticity restoring device 2 is implanted. In at least one embodiment, the connecting member 4 is tapered and has a radial extent or diameter at a first end that is equal to the expanded profile (Pe) of the first fixation member 3a and a radial extent or diameter at a second end that is equal to the expanded profile (Pe) of the second fixation member 3b, where the expanded profile (Pe) of the second fixation member 3b is less than the expanded profile (Pe) of the first fixation member 3a. In other embodiments, the amount of direct contact between the connecting member 4 and the wall of the airway is minimized to reduce rubbing of the connecting member 4 against the airway wall as the connecting member 4 longitudinally expands and contracts. In this embodiment the connecting member 4 has a maximum radial extent that is less than the diameter of the airway.

In at least one embodiment, the connecting member 4 has a maximum longitudinal extent or length of about 21.87 cm and a minimum longitudinal extent or length of about 2 cm. In some embodiments, the length of the connecting member 4 in the stretched state is not more than 50% greater than the length of the connecting member 4 in the rest state. In some embodiments, the connecting member 4 radially expands and contracts due to the longitudinal expansion and contraction of the connecting member 4.

In at least one embodiment, the connecting member 4 radially contracts less than approximately 20% due to the longitudinal elongation of the connecting member 4 during inhalation, and radially expands approximately 20% due to the longitudinal contraction of the connecting member during expiration.

In at least one embodiment, the connecting member 4 reduces migration of the lung elasticity restoring device 2 towards the alveoli. Without being bound by theory, the bias of the connecting member 4 to the rest state reduces migration towards the alveoli. In some embodiments the reduction in the airway diameters also reduces migration towards the alveoli.

In some embodiments, the connecting member 4 when implanted is parallel to internal surface of the airway. In at least one embodiment, the connecting member 4 is deployed in the airway, such that a portion of the airway along the length of the connecting member 4 is uncovered to allow the cilia on the inner wall of the airway to perform its regular functions such as sweeping the mucus up and out of the lungs.

Figure 5A:
FIGS. 5A-F are side views of exemplary tubular connecting members.
Figure 5B:
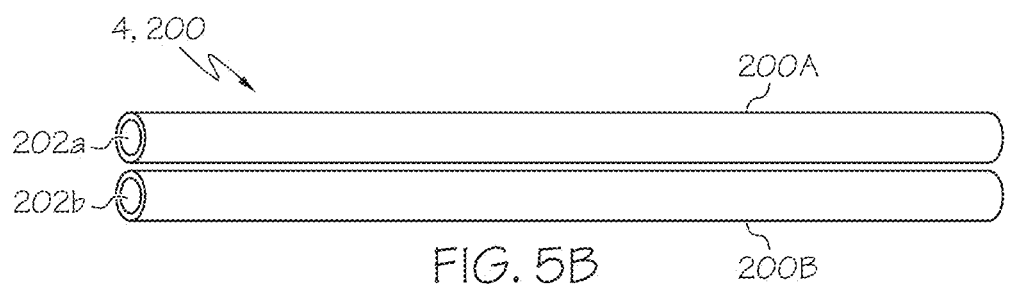

In some embodiments, the connecting member 4 is one or more tubular members. This type of connecting member 4 can be referred to as a tubular connecting member 200. FIGS. 5A and 5C-F show exemplary embodiments of a tubular connecting member 200 that is a single tubular member 200A; and FIG. 5B shows an exemplary embodiment of a tubular connecting member 200 that is formed of two tubular members 200A, 200B. In some embodiments, the two tubular members 200A, 200B are parallel to one another.

In one aspect, the tubular connecting member 200 defines one or more longitudinally extending lumens 202. Air, drug therapies, or medical devices such as a guidewire can traverse through a longitudinally extending lumen 202 of the connecting member 4. As depicted in FIG. 5A, the connecting member 4 is an elongated member 200 that defines a single lumen 202. In some embodiments, a connecting member 4 defining a single lumen 202 covers the entire inner circumferential area of the airway.

Figure 5C:
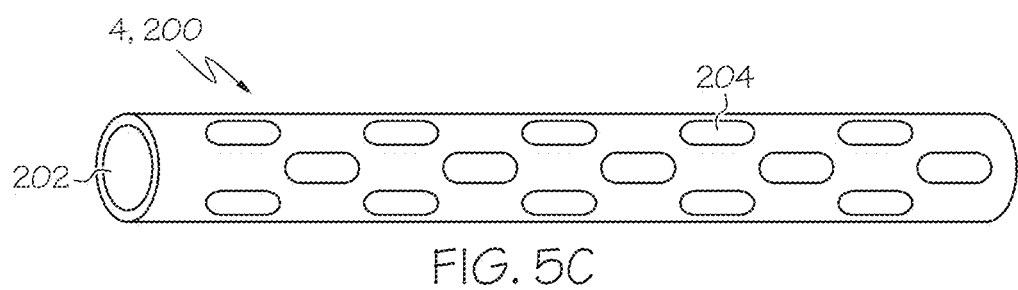
Figure 5D:
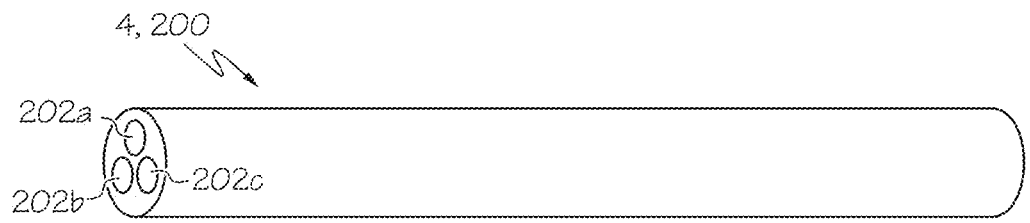
Figure 5E:
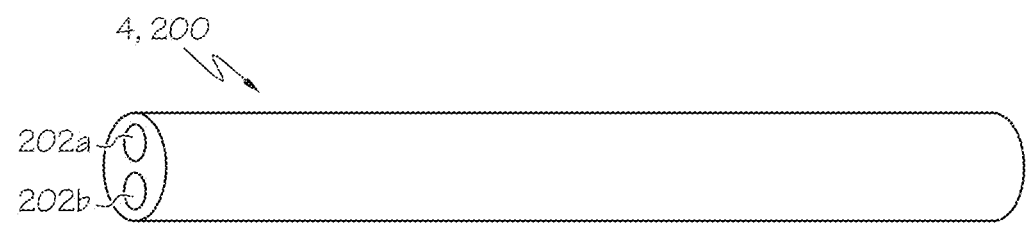

As shown for example in FIG. 5D, the tubular connecting member 200 is an elongated member that defines three lumens 202a, 202b, 202c. In some embodiments, one lumen is provided for drug delivery, a second lumen is used for air traversal, and a third lumen is employed to deliver a guidewire with/without a pressure sensor to a target site. It is noted that air can traverse through the all of the lumens when a lumen is not being used for movement of a drug or guidewire therethrough. As shown for example in FIG. 5E, the connecting member 200 defines two lumens 202a, 202b extending therethrough. In such an instance, one lumen can be provided for drug delivery and other lumen can be provided for traversal of air. Again, when a drug is not being delivered through the lumen, air can flow therethrough.

Figure 5F:
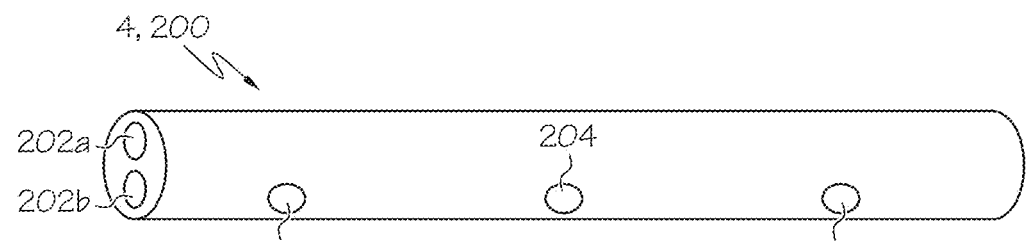

In some embodiments, which may be combined with other aspects of the connecting member 4 described above, the tubular connecting member 200 has one or more holes, such as identified with reference number 204, extending through the wall of the connecting member 4, for example as shown in FIGS. 5C and 5F. In some embodiments, the holes 204 are provided for allowing airflow into/out of the connecting member 4 and into adjacent or branching bronchi/bronchioles. In addition, the holes 204 can provide for drug release through the connecting member 4. In still other embodiments, cilia extend through the holes 204 to perform their function of sweeping the mucus up and out of the lungs. The size of the holes 204 may range in size from about 0.4 cm to about 1.80 cm. The holes 204 can be configured in any pattern, including regular or irregular patterns. The holes 204 can be of any symmetrical or unsymmetrical shape. In some embodiments, the holes 204 provide for areas of the airway to be uncovered by the connecting member 4 so that the entire circumferential area is not covered by the connecting member 4.

Figure 6:
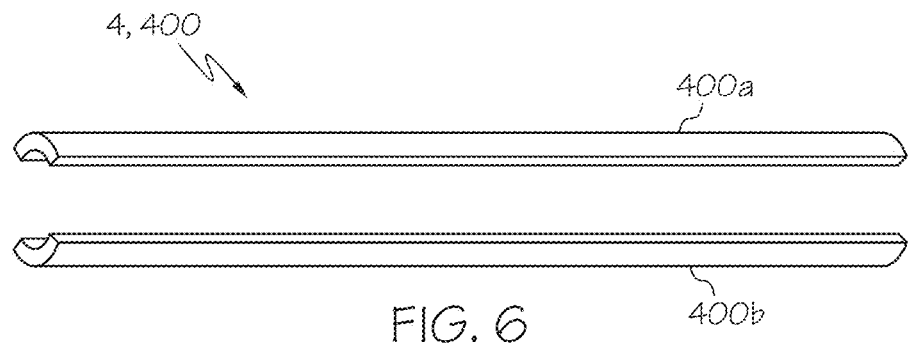
FIG. 6 is a side view of an exemplary band connecting member.

In some embodiments, the connecting member 4 is one or more bands 400. This type of connecting member 4 can be referred to as a band connecting member 400. In at least one embodiment, for example as shown in FIG. 6, the connecting member 4 is two bands 400 (such as 400A, 400B). In some embodiments, each band 400A, 400B has an arcuate shape or a C-shaped structure.

Figure 7:
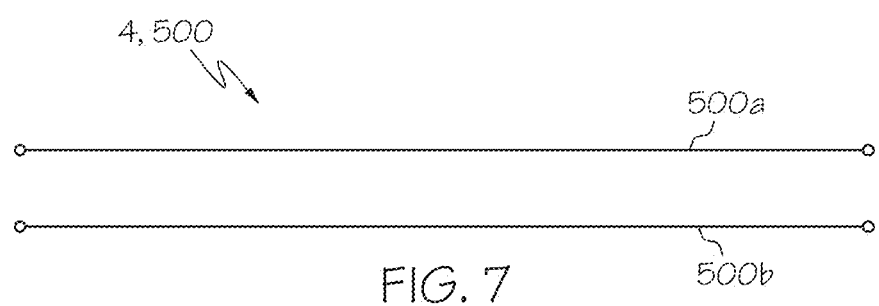
FIG. 7 is a side view of an exemplary cord/wire connecting member.

In some embodiments, the connecting member 4 is one or more cords or wires 500, as shown for example in FIG. 7. These types of connecting members 4 can respectively be referred to as a cord connecting member 500 or a wire connecting member 500. The cord or wire can be formed of a number of filaments (multi-filament) or be a single filament (monofilament). The cross-sectional shape of the filament can be round, rectangular, oval, or square. In at least one embodiment, the cord or wire is a coil spring (not shown). This type of connecting member 4 can be referred to as a coil spring connecting member. In this embodiment, the connecting member 4 has the coil configuration in both the rest state and the stretched state. A coil spring connecting member is an example of a connecting member with a uniform longitudinal length but different longitudinal extents in the rest state and the stretched state. In one embodiment, the diameter of the coil spring is less than the diameter of the airway to decrease the potential for the connecting member to rub against the airway wall as the connecting member lengthens and contracts.

Figure 8:
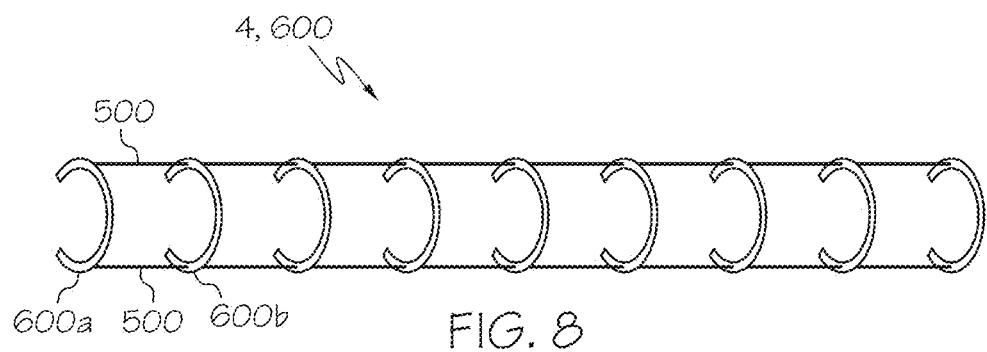
FIG. 8 is a side view of an exemplary interconnected C-shaped connecting member.

In at least one embodiment the connecting member 4 can be formed of interconnected structures 600. As shown in FIG. 8, the connecting member 4 includes a number of interconnected C-shaped structures 600. The C-shaped structures 600 can be interconnected by band(s) 400, cord(s) 500, wire(s) 500, or any other elastic membrane. In some embodiments, the C-shaped structures 600 are fixed to a braided mesh structure of wires and/or cords.

C. Valve

The lung elasticity restoring device 2 may further include a valve 46 constructed and arranged to partially close thereby partially occluding the lumen of the lung elasticity restoring device 2. The valve 46 may form a part of a fixation member 3 or a connecting member 4. Alternatively, the valve 46 may be a separate member positioned inside the lumen of a fixation member 3 or a connecting member 4. A valve 46 in the form of a separate member positioned inside the lumen of a fixation or connecting member 3, 4, may be secured in an inner surface of the fixation or connecting member 3, 4. Preferably, the valve 46 is positioned in, or form a part of, the proximal fixation member 3a of a lung elasticity restoring device 2. However, a valve 46 may alternatively or additionally be positioned in, or form a part of, a connecting member 4 and/or a distal fixation member 3b.

The valve 46 partially closes during exhalation/expiration, thereby partially occluding the lumen of the lung elasticity device 2, while during inhalation, the valve 46 is open and does not occlude the lumen of the lung elasticity device 2. Thus, when the lung elasticity restoring device is implanted, the valve 46 can be described as having a partially closed configuration during exhalation/expiration and an open configuration during inhalation. Without being bound by theory, by partially closing on exhalation, the distal airways are held open due to the slight increase in the air pressure slightly distal to the valve 46. This may be useful to treat conditions where the distal airways close during exhalation thereby trapping air, e.g. COPD. Thus in some embodiments, a valve 46 may facilitate deflation of the lung 902.

The valve 46 in the partially closed configuration may be described as being angled toward the alveoli and away from the trachea. The angle θ of the valve 46 in the partially closed configuration is less than 90°, preferably no more than 45°, relative to the longitudinal axis of the lung elasticity restoring device 2 (see e.g. FIG. 14). When the valve 46 is in the open configuration, the valve 46 is oriented parallel to the longitudinal axis of the lung elasticity restoring device 2. Thus, the valve 46 may be described as moving towards the trachea as the valve 46 transitions from the open configuration to the partially closed configuration.

Any suitable valve may be used for the valve 46 so long as it constructed and arranged to partially occlude the lumen of the lung elasticity device 2 as described herein.

D. Respiration Assistance Member

In a further aspect, the lung elasticity restoring device 2 includes a respiration assistance member 5 (see e.g. FIG. 13). In at least one embodiment, the respiration assistance member 5 defines one or more longitudinally extending lumens, each lumen having an open proximal end. In some embodiments, the lumen has an open distal end. In other embodiments, the lumen has a closed distal end.

In some embodiments, the respiration assistance member 5 is an extension of the tubular connecting member 200 discussed above. In another embodiment, the respiration assistance member 5 is one lumen of a lumen connecting member 4 discussed above. In other embodiments, the respiration assistance member 5 extends the length of the lung elasticity restoring device 2.

In other embodiments, the respiration assistance member 5 is a separate member from the connecting member 4. In one embodiment, the distal end of the respiration assistance member 5 connected to the proximal fixation member 3a of the lung elasticity restoring device 2. In this embodiment, the respiration assistance member 5 extends only to the proximal fixation member 3a of the lung elasticity restoring device 2. This is shown for example by the respiration assistance member 5 schematically shown in FIG. 13. The proximal fixation member 3a may be implanted in the trachea or in a bronchiole. In another embodiment, the respiration assistance member 5 is secured to an inner surface of the connecting member 4.

In some embodiments, the respiration assistance member 5 is a single lumen member. In some embodiments, the lumen has a diameter equal to, or less than, the diameter of the trachea. In one embodiment the lumen has a diameter of about 1.80 cm.

In other embodiments, the respiration assistance member 5 is a multi-lumen member that has an inflation/deflation lumen for inflation/deflation of a balloon fixation member 100 and a separate respiration assistance lumen in fluid communication with the external device. In this embodiment, the respiration assistance member 5 is engaged to each of the balloon fixation members 100 of the lung elasticity restoring device 2. In one embodiment, the lumen for inflation/deflation is sized for the detachable inflation mechanism 102 described above.

In at least one embodiment, a therapeutic agent is administered to the airway through the respiration assistance member 5. Examples of therapeutic agents that may be administered are disclosed below.

In at least one embodiment, the respiration assistance member 5 is in communication with an external device when the lung elasticity restoring device 2 is implanted. External devices include but are not limited to, an external oxygen supply, a breathing assistance device, or a nebulizer. Examples of external oxygen supplies include oxygen tanks and oxygen concentrators. A non-limiting example of a breathing assistance device is a positive airway pressure ventilator such as a continuous positive airway pressure (CPAP) machine or a bilevel positive airway pressure (BPAP) machine. Positive airway pressure ventilators are often used for chronic conditions such as sleep apnea or COPD.

In at least one embodiment, the respiration assistance member 5 exits the body through an incision made in the tracheal wall and is connected to the external device.

In at least one embodiment, the respiration assistance member 5 is connected to a tracheostomy tube or a tracheal button. As used herein, a "tracheostomy tube" is a curved metal or plastic tube inserted into a tracheostomy stoma to maintain a patent lumen, and a "tracheal button" is a rigid tube placed into the tracheostomy after removal of the tracheostomy tube to maintain patency of the lumen. Typically, the tracheal button is shorter than the tracheostomy tube. In some embodiments, the tracheostomy tube or the tracheal button is connected to the external device. For example, a tube connects the tracheostomy tube or the tracheal button to the external device.

In some embodiments, the lung elasticity restoring device 2 is connected to the tracheostomy tube or the tracheal button as part of implanting the lung elasticity restoring device 2. For example, the outer surface of the proximal end region of the respiration assistance member 5 has an adhesive for attachment to an inner surface of the tracheostomy tube or the tracheal button.

In a further aspect, the tracheostomy tube or the tracheal button forms a part of the lung elasticity restoring device 2. In this embodiment, the lung elasticity restoring device 2 is implanted when the tracheostomy tube or tracheal button is implanted.

In some embodiments, the respiration assistance member 5 is connected to a nasal cannula. As used herein, a "nasal cannula" is a device used to delivery supplemental oxygen or airflow to a person and includes a tube connected to an oxygen supply, the tube has two prongs each placed in a nostril and from which air/oxygen flows. In one embodiment, the respiration assistance member 5 is connected to one or both prongs of the nasal cannula. For embodiments where the respiration member 5 is connected to both prongs of a nasal cannula, the proximal end region of the respiration assistance member 5 is bifurcated.

In other embodiments, the respiration assistance member 5 has a tubular proximal end region sized for a nasal passage. In this embodiment, the respiration assistance member 5 exits the body from the nose and is connected to the external device.

In at least one embodiment, the respiration assistance member 5 includes one or more holes such as discussed above for the connecting member 4. In one embodiment, the holes of the respiration assistance member 5 are aligned with holes 204 of the connecting member 4.

E. Suitable Materials; Coverings; Therapeutic Agents

The fixation, connecting members, and respiration assistance members 3, 4, 5 can be made from any flexible, elastic, and biocompatible material, so that they can be easily fit into the airways and are able to expand up to their elasticity limits. In some embodiments, the stent fixation member 8 can be formed using NiTi, SST, Elgiloy, and elastic polymers. The connecting member 4 and the respiration assistance member 5 can be formed using materials such as, but not limited to SIBS, latex, silicone, polyurethane, co-polymers, or a combination of any of these. Other suitable examples of polymers for making the connecting member 4 or the respiration assistance member 5 include polytetrafluoroethylene (PTFE), ethylene tetrafluoroethylene (ETFE), perfluoroalkoxy (PFA), polyether ether ketone (PEEK), high density polyethylene (HDPE), polypropylene (PP), and so forth.

Superelastic materials such as NiTi and Elgiloy are also suitable for manufacturing the stent fixation member 8, and/or the connecting member 4 of the lung elasticity restoring device 2. In one embodiment, the cord or wire connecting members 500 comprise a superelastic material.

Examples of suitable biocompatible materials include biodegradable materials that are also biocompatible. Biodegradable in this case is intended to mean or otherwise include a material that undergoes a breakdown or decomposition into harmless compounds as part of a normal biological process. Suitable biodegradable materials include magnesium, iron, polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers.

Non-limiting examples suitable materials for the cover or liner of the fixation member 3 include, but are not limited to, ePTFE, silicone elastomers, polyurethane, polystyrene-polyisobutylene-polystyrene triblock copolymer (SIBS), and combinations thereof.

In at least one embodiment, the balloon 104 of the balloon fixation member 100 is made of a biocompatible material. In at least one embodiment, the balloon 104 is manufactured from a polymeric material. In at least one embodiment, the balloon 104 is manufactured from a compliant material for example, but not limited to, nylon, silicones, and polyamines. In at least one embodiment, the balloon 104 is manufactured from a semi-compliant material, for example, but not limited to, ethylene-vinyl acetate, olefin copolymers or homopolymers, polyethylenes, polyurethanes, cross-linked low density polyethylenes (PETs), highly irradiated linear low density polyethylene (LDPE), acrylonitrile polymers and copolymers, acrylonitrile blends and ionomer resins. In at least one embodiment, the balloon 104 is manufactured from a non-compliant material, for example, but not limited to, polyethylene terephthalates, polyacrylenesulfide, polyoxymethylene and polyoxymethylene copolymers, and polyesters and polyester copolymers. Other materials may also be used for the balloon 104 including, but not limited to, polyvinyl chloride (PVC), and polyacrylenesulfide copolyesters.

The lung elasticity restoring device 2 can include one or more coatings or other layers of therapeutic agent placed on surface regions of the fixation, connecting and/or respiration assistance members 3, 4, 5, adapted to be released at the site of the fixation, connecting, and/or respiration assistance members' implantation or areas adjacent thereto.

A therapeutic agent may be a drug or other pharmaceutical product, such as non-genetic agents, genetic agents, cellular material, etc. Some examples of suitable non-genetic therapeutic agents include, but are not limited to: bronchodilators, such as albuterol, levalbuteral, ipratropium tiotropium, salmeterol, formoterol, arformoterol, indacaterol, aclidinium, glycopyrronium, darotropium; steroids such as bluticasone and budesonide; combinations of bronchodilators and steroids; phosphodiesterase-4 inhibitors; theophylline; ultra long acting muscarinic antagonists (ultra-LAMA); ultra long acting $\beta_2$ agonists (ultra-LABA); antibiotics; anti-inflammatory drugs; matrix metalloproteinases (MMP) inhibitors; tumor necrosis factor-$\alpha$ inhibitors; transforming growth factor (TGF)-$\beta$ inhibitors; anti-thrombogenic agents, such as heparin, heparin derivatives; vascular cell growth promoters; and growth factor inhibitors, Paclitaxel, etc. Where an agent includes a genetic therapeutic agent, such a genetic agent may include, but is not limited to: DNA, RNA and their respective derivatives and/or components; hedge-hog proteins, etc. Where a therapeutic agent includes cellular material, the cellular material may include, but is not limited to: cells of human origin and/or derivatives thereof, including stem cells. Where the therapeutic agent includes a polymer agent, the polymer agent may be a polystyrene-polyisobutylene-polystyrene triblock copolymer (SIBS), polyethylene oxide, silicone rubber and/or any other suitable substrate.

F. Lung Elasticity Restoring Device

In at least one embodiment, the lung elasticity restoring device 2 has an inspiration configuration and an expiration configuration. The lung elasticity restoring device 2 is configured to move reversibly between the inspiration configuration and the expiration configuration. The configuration of the lung elasticity restoring device 2 depends on the state of the connecting member 4. As discussed above, when the air is inhaled into the lungs, the air can cause the airways to expand thereby longitudinally expanding the connecting member 4, as shown in FIGS. 10 and 11A. Thus, during inhalation, the lung elasticity restoring device 2 expands to the inspiration configuration where the connecting member 4 moves to the stretched state and the fixation members 3a, 3b are in the expanded state (Pe). During exhalation of air from the lungs, the lung elasticity restoring device 2 contracts to the expiration configuration where the connecting member 4 retracts to the rest state and the fixation members 3a, 3b, are in the expanded state (Pe). Hence, the lung elasticity restoring device 2 is biased to the expiration configuration because of the stretched connecting member 4.

As discussed above, the lung elasticity restoring device 2 may include a valve 46. Where the lung elasticity restoring device 2 includes a valve 46, the valve 46 is open when the lung elasticity restoring device 2 is in the inspiration configuration and partially closed when the lung elasticity restoring device 2 is in the expiration configuration.

In at least one embodiment, the lung elasticity restoring device 2 is delivered to an implantation site via a bronchoscope or a delivery catheter. In at least one embodiment, the lung elasticity restoring device 2 is delivered to an airway in a delivery configuration. In some embodiments, when the lung elasticity restoring device 2 is in the delivery configuration the fixation members 3 are in the delivery state (Pd) and the connecting member 4 is in the stretched state. In this embodiment, since the connecting member 4 is biased to the rest state, the lung elasticity restoring device 2 moves the lung towards its compressed expiration state upon implantation. In other embodiments, the connecting member 4 may be straight or folded between the fixation members 3 which are in the delivery state (Pd).

As discussed below, the lung elasticity restoring device 2 may be deployed only in the conducting zone, i.e., bronchioles; only in the non-conducting zone; or in both the conducting and the non-conducting zones. As used herein, the "conducting zone" comprises the trachea, bronchi, bronchioles, and terminal bronchioles of a lung; and the "non-conducting zone" comprises respiratory bronchioles, alveolar ducts, and alveolar sacs of a lung. For example, the fixation and connecting members 3, 4 may be deployed in the trachea, bronchi, bronchioles, terminal bronchioles, respiratory bronchioles, alveolar ducts, etc.

In some embodiments, the expanded profile (Pe) of the fixation member 3 and the radial extent of the connecting member 4 corresponds to the diameter of the location where the fixation and connecting members 3, 4 are to be deployed. Likewise, the length of the connecting member 4 depends upon where the fixation members 3 are to be deployed. Thus, for example, a portion of the lung elasticity restoring device 2 that is configured to be implanted in the trachea would have a radial extent of 1.80 cm and a portion of the lung elasticity restoring device 2 that is configured to be implanted in a bronchiole has a radial extent of 0.45 cm. Sizes of different portions of the respiratory system are as follows:

| S. No. | Different Portions of respiratory system | Generation | Diameter (cm) | Length (cm) |
|---|---|---|---|---|
| (A) Conducting Zone | | | | |
| 1 | Trachea | 0 | 1.80 | 12.0 |
| 2 | Bronchi | 1 | 1.22 | 4.8 |
| 3 | Bronchi | 2 | 0.83 | 1.9 |
| 4 | Bronchi | 3 | 0.56 | 0.8 |
| 5 | Bronchioles | 4 | 0.45 | 1.3 |
| 6 | Terminal Bronchioles | 5 to 16 | 0.35 to 0.06 | 1.07 to 0.17 |
| (B) Transitional and Respiratory Zones | | | | |
| 1 | Respiratory Bronchioles | 17 | Till 0.05 | Till 0.10 |
| 2 | Respiratory Bronchioles | 18 | Till 0.05 | Till 0.10 |
| 3 | Respiratory Bronchioles | 19 | Till 0.05 | Till 0.10 |
| 4 | Alveolar Ducts | 20 | >0.04 and <0.05 | >0.10 and <0.05 |
| 5 | Alveolar Ducts | 21 | >0.04 and <0.05 | >0.10 and <0.05 |
| 6 | Alveolar Ducts | 22 | >0.04 and <0.05 | >0.10 and <0.05 |
| 7 | Alveolar Sacs | 23 | 0.04 | 0.05 |

Some exemplary implantation configurations of a lung elasticity restoring device 2 are shown in FIGS. 11-13. As noted above, the lung elasticity restoring device 2 can be implanted to help expel air from one lung or from both lungs.

FIGS. 11A-B show a lung elasticity restoring device 2 deployed in one lung 902. The lung elasticity restoring device 2 includes a connecting member 4, extending between a first fixation member 3a, and a second fixation member 3b. The first fixation member 3a is implanted at a proximal fixation point, and the second fixation member 3b is implanted at a distal fixation point. Thus, the fixation members 3a, 3b are sized for their respective implantation sites in the lung 900. As shown in FIG. 11A, the proximal fixation point is the trachea and the distal fixation point is a bronchiole. However, the fixation points or implantation sites, for the fixation members 3 can both be in a bronchiole of one lung 900. For example, the first, proximal fixation point can be at a $7^{th}$ generation bronchiole, and the second, distal fixation point can be at a $12^{th}$ generation bronchiole. The first fixation member 3a has a first expanded profile (Pe) or diameter, and the second fixation member 3b has a second expanded profile (Pe) or diameter that can be different from the first expanded profile (Pe) depending on the diameter of the implantation site.

FIG. 11A shows the lung elasticity restoring device 2 in the inspiration configuration with the connecting member 4 in the stretched state, and FIG. 11B shows the lung elasticity restoring device 2 in the expiration configuration with the connecting member 4 in the rest state. Since the connecting member 4 is biased towards the rest state, the connecting member 4 will collapse or contract to the rest state thereby causing the lung 900 to partially collapse or contract, thereby restoring elasticity to a diseased lung 900. The collapse of the lung 900 causes the air to be exhaled.

Also, because the connecting member 4 contracts to the rest state, the lung elasticity restoring device 2 has a greater extent in the inspiration configuration as compared to the extent in the expiration configuration. As the lung elasticity restoring device 2 moves from the inspiration configuration to the expiration configuration, the position of the second fixation member 3b relative to that of the first fixation member 3a changes due to expansion and contraction of the connecting and fixation members 3. However, as discussed above the lung elasticity restoring device 2 is configured so that the positions of the fixation members 3 in the airway do not change as the lung elasticity restoring device 2 expands and contracts.

In some embodiments, the first fixation member 3a and the second fixation member 3b are implanted in different lungs 900a, 900b, as shown in FIG. 12. With this implantation configuration, the lung elasticity restoring device 2 contracts the lungs by bringing the two lungs 900a, 900b closer together help expel air from both lungs 900a, 900b. Again, the expanded profiles (Pe) of the fixation members 3a, 3b correspond to the sizes of airways of the left and right lungs 900a, 900b, respectively. Further, the connecting member 4 of the lung elasticity restoring device 2 has holes 204 sized for air to flow into and out of the connecting member (not shown in FIG. 12). For example, the connecting member 4 shown in FIG. 12 has at least six holes, with one hole 204 being sized for the trachea to allow air to flow from the trachea into the connecting member 4 and the other holes 204 being sized for the different bronchioles spanned by the connecting member 4.

In some embodiments, for example as shown in FIG. 13, the lung elasticity restoring device 2 is bifurcated and has three fixation members 3a, 3b, 3c. In one embodiment, the connecting member 4 of a bifurcated lung elasticity restoring device 2 includes a trunk 962, a first leg 966, and a second leg 968, as shown in FIG. 13.

Again, although not shown in the schematic representation of the lung elasticity restoring device 2 provided in FIG. 13, the connecting member 4 includes holes 104 for air to flow into and out of the connecting member 4 and into and out of the branch airways. In another embodiment, a first connecting member extends from and connects the first fixation member 3a and the second fixation member 3b and a second connecting member 4a extends from and connects the first fixation member 3a and the third fixation member 3b (not shown).

As shown in FIG. 13, a cover extends beyond the fixation members 3b, 3c to form the distal ends of the lung elasticity restoring device 2. However, in some embodiments the cover does not extend beyond the ends of the fixation members 3. In these embodiments, the second fixation member 3b forms an end of the first leg 966, and the third fixation member 3c forms an end of the second leg 968.

As discussed above, FIG. 13 also schematically shows a respiration assistance member 964 extending proximally from the first fixation member 3a.

The lung elasticity restoring device 2 shown in FIG. 13 is implanted so that the first fixation member 3a, defining a first expanded profile (Pe), is implanted in the trachea 950, the second fixation member 3b, defining a second expanded profile (Pe), is implanted in a bronchiole 952 of one lung 900a, and a third fixation member 3c, defining a third expanded profile (Pe), is implanted in a bronchiole 954 of the other lung 900b. Each of the fixation members 3a, 3b, 3c is anchored firmly at fixation points. A lung elasticity restoring device 2 implanted as shown in FIG. 13 longitudinally contracts the lungs to help expel the air from both lungs 900a, 900b. The fixation members 3 of a bifurcated lung elasticity restoring device 2 can be deployed either at different positions in a same lung 900 or different lungs 900a, 900b. For example, the fixation members 3 of the legs of a bifurcated lung elasticity restoring device 2 can be implanted for example in two $12^{th}$ generation bronchioles and the fixation member 3 of the trunk can be implanted in a $7^{th}$ generation bronchiole (not shown).

The embodiments or aspects of the lung elasticity restoring device 2, including the embodiments presented in the claims, may be combined in any fashion and combination and be within the scope of the present disclosure. As a non-limiting example, the following embodiments or aspects of the lung elasticity restoring device 2 may be combined in any fashion and combination and be within the scope of a lung elasticity restoring device 2 disclosed herein, as follows:

Aspect 1. A lung elasticity restoring device configured to be deployed in an airway, the lung elasticity restoring device comprising:
fixation members, the fixation members comprising:
a first radially expandable fixation member having a first profile in an expanded state and defining a lumen; and
a second radially expandable fixation member having a second profile in an expanded state and defining a lumen;
a connecting member extending between and connecting the first and second fixation members;
the lung elasticity restoring device being reversibly extendable between an inspiration configuration and an expiration configuration, the lung elasticity restoring device being extendable to the inspiration configuration and biased to the expiration configuration, the lung elasticity restoring device being biased to the expiration configuration by the connecting member.

Aspect 2. The lung elasticity restoring device of aspect 1, wherein the fixation members are selected from the group consisting of: stents and balloons.

Aspect 3. The lung elasticity restoring device of aspect 2, wherein the first fixation member is a stent and the second fixation member is a stent.

Aspect 4. The lung elasticity restoring device of aspect 2, wherein the first fixation member is a stent and the second fixation member is a balloon.

Aspect 5. The lung elasticity restoring device of aspect 2, wherein the first fixation member is a balloon and the second fixation member is a balloon.

Aspect 6. The lung elasticity restoring device of aspects 1-5, the connecting member being elastic or super elastic, wherein the connecting member is selected from a group consisting of:
a tubular member defining at least one longitudinal lumen;
a band;
a cord;
a wire; and
interconnected support structures.

Aspect 7. The lung elasticity restoring device of aspect 6, wherein the connecting member is the tubular member defining at least one longitudinal lumen.

Aspect 8. The lung elasticity restoring device of aspects 6-7, wherein the tubular member is a single tubular member.

Aspect 9. The lung elasticity restoring device of aspects 6-7, wherein the tubular member is two tubular members.

Aspect 10. The lung elasticity restoring device of aspects 6-7, wherein the two tubular members parallel one another.

Aspect 11. The lung elasticity restoring device of aspects 6-8, wherein the tubular member defines a single longitudinal lumen.

Aspect 12. The lung elasticity restoring device of aspects 9-10, wherein each of the two tubular members defines a single longitudinal lumen.

Aspect 13. The lung elasticity restoring device of aspects 6-7, wherein the tubular member defines two longitudinal lumens.

Aspect 14. The lung elasticity restoring device of aspect 6-7, wherein the tubular member defines three longitudinal lumens.

Aspect 15. The lung elasticity restoring device of aspects 7-14, wherein the tubular member further defines at least one side hole extending through a wall of the tubular member.

Aspect 16. The lung elasticity restoring device of aspect 6, wherein the connecting member is the band.

Aspect 17. The lung elasticity restoring device of aspect 6, wherein the connecting member is the cord.

Aspect 18. The lung elasticity restoring device of aspect 6, wherein the connecting member is the wire.

Aspect 19. The lung elasticity restoring device of aspect 6, wherein the connecting member is the interconnected support structures.

Aspect 20. The lung elasticity restoring device of aspect 19, wherein the interconnected support structures are semi-tubular.

Aspect 21. The lung elasticity restoring device of aspects 19-20, wherein the interconnected support structures are C-shaped.

Aspect 22. The lung elasticity restoring device of aspects 6 and 19-21, wherein the interconnected support structures are interconnected by a band, a cord, or a wire.

Aspect 23. The lung elasticity restoring device of aspect 22, wherein the interconnected support structures are interconnected by the band.

Aspect 24. The lung elasticity restoring device of aspect 22, wherein the interconnected support structures are interconnected by the cord.

Aspect 25. The lung elasticity restoring device of aspect 22, wherein the interconnected support structures are interconnected by the wire.

Aspect 26. The lung elasticity restoring device of aspects 2-4 and 6-25, wherein the stents are selected from the group consisting of:
tubular stents;
semi-tubular stents; and
stents with radial members extending from a longitudinal core.

Aspect 27. The lung elasticity restoring device of aspects 3 and 6-26, wherein the first fixation member is a tubular stent and the second fixation member is a tubular stent.

Aspect 28. The lung elasticity restoring device of aspects 3 and 6-26, wherein the first fixation member is a tubular stent and the second fixation member is a semi-tubular stent.

Aspect 29 The lung elasticity restoring device of aspects 3 and 6-26, wherein the first fixation member is a tubular stent and the second fixation member is a stent with radial members extending from a longitudinal core.

Aspect 30. The lung elasticity restoring device of aspects 3 and 6-26, wherein the first fixation member is a semi-tubular stent and the second fixation member is a semi-tubular stent.

Aspect 31. The lung elasticity restoring device of aspects 3 and 6-26, wherein the first fixation member is a semi-tubular stent and the second fixation member is a stent with radial members extending from a longitudinal core.

Aspect 32. The lung elasticity restoring device of aspects 3 and 6-26, wherein the first fixation member is a stent with radial members extending from a longitudinal core and the second fixation member is a stent with radial members extending from a longitudinal core.

Aspect 33. The lung elasticity restoring device of aspects 4 and 6-26, wherein the stent is a tubular stent.

Aspect 34. The lung elasticity restoring device of aspects 4 and 6-26, wherein the stent is a semi-tubular stent.

Aspect 35. The lung elasticity restoring device of aspects 4 and 6-26, wherein the stent is a stent with radial members extending from a longitudinal core.

Aspect 36 The lung elasticity restoring device of aspects 1-35, wherein the expanded state of the first radially expandable fixation member is sized for a first airway, and the expanded state of the second radially expandable fixation member is sized for a second airway; the lung elasticity restoring device extending from the first airway into the second airway when implanted.

Aspect 37. The lung elasticity restoring device of aspects 1-36 the first fixation member forming a first end of the lung elasticity restoring device, and the second fixation member forming a second end of the lung elasticity restoring device.

Aspect 38. The lung elasticity restoring device of aspects 1-37, further comprising a third radially expandable fixation member having a third profile in an expanded state, wherein the expanded state of the third radially expandable fixation member is sized for a third airway;
the lung elasticity restoring device being a bifurcated device comprising a trunk, a first leg and a second leg, wherein the first radially expandable fixation member forms an end of the trunk, the second radially expandable fixation member forms an end of the first leg and the third radially expandable fixation member forms an end of the second leg.

Aspect 39. The lung elasticity restoring device of aspects 37-38, the first, second, and third airways being different airways, the airways selected from the group consisting of a trachea, a bronchus, and a bronchiole.

Aspect 40. The lung elasticity restoring device of aspects 1-39, wherein the expanded state of the first radially expandable fixation member is sized for an airway of a left lung and the expanded state of the second radially expandable fixation member is sized for an airway of a right lung.

Aspect 41. The lung elasticity restoring device of aspects 1-40 wherein the fixation devices do not penetrate a wall of the airways.

Aspect 42. The lung elasticity restoring device of aspects 1-41, wherein the fixation devices comprise protrusions extending at an oblique angle from an outer surface of the fixation device, the protrusions being oriented away from the alveoli when the lung elasticity restoring device is implanted, the protrusions configured to anchor the fixation devices in the airway.

Aspect 43. The lung elasticity restoring device of aspects 1-42, wherein the lung elasticity restoring device has a greater extent in the inspiration configuration than in the contracted expiration configuration.

Aspect 44. The lung elasticity restoring device of aspect 1-43, wherein the second radially expandable fixation member has a first position relative to the first radially expandable fixation member when the lung elasticity restoring device is in the inspiration configuration; and the second radially expandable fixation member has a second position relative to the first radially expandable fixation member when the lung elasticity restoring device is in the expiration configuration, the second position of the second radially expandable fixation member being different than the first position.

Aspect 44. A lung elasticity restoring device comprising:
a first stent having a first profile in an expanded state, the first stent forming a first end of the lung elasticity restoring device;
a second stent having a second profile in an expanded state, the second stent forming a second end of the lung elasticity restoring device;
a connecting member extending between and connecting the first and second stents, the connecting member being elastic or superelastic and having a rest state and a stretched state;
the lung elasticity restoring device being reversibly extendable between an inspiration state and an expiration state, the lung elasticity restoring device being expandable to the inspiration state and biased to the expiration state by the connecting member, the connecting member being in the rest state when the lung elasticity restoring device is in the expiration state and the connecting member being in the stretched state when the lung elasticity restoring device in the inspiration state.

Aspect 45. The lung elasticity restoring device of aspect 44, wherein the first and second stents are selected from the group consisting of:
tubular stents;
semi-tubular stents; and
stents with radial members extending from a longitudinal core.

Aspect 46. The lung elasticity restoring device of aspects 45, wherein the first stent is a tubular stent and the second stent is a tubular stent.

Aspect 47. The lung elasticity restoring device of aspects 45, wherein the first stent is a tubular stent and the second stent is a semi-tubular stent.

Aspect 48 The lung elasticity restoring device of aspects 45, wherein the first stent is a tubular stent and the second stent is a stent with radial members extending from a longitudinal core.

Aspect 49. The lung elasticity restoring device of aspects 45, wherein the first stent is a semi-tubular stent and the second stent is a semi-tubular stent.

Aspect 50. The lung elasticity restoring device of aspects 45, wherein the first stent is a semi-tubular stent and the second stent is a stent with radial members extending from a longitudinal core.

Aspect 51. The lung elasticity restoring device of aspects 45, wherein the first stent is a stent with radial members extending from a longitudinal core and the second stent is a stent with radial members extending from a longitudinal core.

Aspect 52. The lung elasticity restoring device of aspects 37-51, wherein the connecting member is selected from a group consisting of:
a tubular member defining at least one longitudinal lumen;
a band;
a cord;
a wire; and
interconnected support structures.

Aspect 53. The lung elasticity restoring device of aspect 52, wherein the connecting member is the tubular member defining at least one longitudinal lumen.

Aspect 54. The lung elasticity restoring device of aspects 52-53, wherein the tubular member is a single tubular member.

Aspect 55. The lung elasticity restoring device of aspects 52-53, wherein the tubular member is two tubular members.

Aspect 56. The lung elasticity restoring device of aspects 52-53, wherein the two tubular members parallel one another.

Aspect 57. The lung elasticity restoring device of aspects 51-53, wherein the tubular member defines a single longitudinal lumen.

Aspect 58. The lung elasticity restoring device of aspects 55-56, wherein each of the two tubular members defines a single longitudinal lumen.

Aspect 59. The lung elasticity restoring device of aspects 52-54, wherein the tubular member defines two longitudinal lumens.

Aspect 60. The lung elasticity restoring device of aspect 52-54, wherein the tubular member defines three longitudinal lumens.

Aspect 61. The lung elasticity restoring device of aspects 52-60, wherein the tubular member further defines at least one side hole extending through a wall of the tubular member.

Aspect 62. The lung elasticity restoring device of aspect 52, wherein the connecting member is the band.

Aspect 63. The lung elasticity restoring device of aspect 52, wherein the connecting member is the cord.

Aspect 64. The lung elasticity restoring device of aspect 52, wherein the connecting member is the wire.

Aspect 65. The lung elasticity restoring device of aspect 52, wherein the connecting member is the interconnected support structures.

Aspect 66. The lung elasticity restoring device of aspect 65, wherein the interconnected support structures are semi-tubular.

Aspect 67. The lung elasticity restoring device of aspect 66, wherein the interconnected support structures are C-shaped.

Aspect 68. The lung elasticity restoring device of aspects 65-67, wherein the interconnected support structures are interconnected by a band, a cord, or a wire.

Aspect 69. The lung elasticity restoring device of aspect 68, wherein the interconnected support structures are interconnected by the band.

Aspect 70. The lung elasticity restoring device of aspect 68, wherein the interconnected support structures are interconnected by the cord.

Aspect 71. The lung elasticity restoring device of aspect 68, wherein the interconnected support structures are interconnected by the wire.

Aspect 72. The lung elasticity restoring device of aspects 44-71, wherein the connecting member is elastic and axially elongates from the rest state to the stretched state.

Aspect 73. The lung elasticity restoring device of aspects 44-72, wherein the connecting member is superelastic and has a different shape in the rest state than in the stretched state.

Aspect 74. The lung elasticity restoring device of aspects 44-73, wherein the first profile has a greater extent than the second profile.

Aspect 75. The lung elasticity restoring device of aspects 6, 17-18, 22, 24-25, 52, 63-64, 68 and 70-71, wherein the cord or wire is a monofilament.

Aspect 76. The lung elasticity restoring device of aspects 6, 17-18, 22, 24-25, 52, 63-64, 68 and 70-71, wherein the cord or wire is a multifilament.

Aspect 77. The lung elasticity restoring device of aspects 2 and 4-5 wherein the balloon has a rough outer surface.

Aspect 78. The lung elasticity restoring device of aspect 77, wherein the rough outer surface is provided by texturing.

Aspect 79. The lung elasticity restoring device of aspect 77, wherein the rough outer surface is provided by protrusions.

Aspect 80. The lung elasticity restoring device of aspects 2, 4-5, and 77-79, wherein the balloon includes an inflation valve.

Aspect 81. The lung elasticity restoring device of aspects 2, 4-5, and 77-80, wherein the balloon is made of a polymeric material.

Aspect 82. The lung elasticity restoring device of aspect 81, wherein the balloon the polymeric material is selected from the group consisting of compliant material, semi-compliant material, or non-compliant material.

Aspect 83. The lung elasticity restoring device of aspects 2, 4-5, and 77-82, wherein the balloon defines an inflation lumen.

Aspect 84. The lung elasticity restoring device of aspects 2-4, 26-35, and 44-51, wherein the stent has a plurality of openings through a stent wall.

Aspect 85. The lung elasticity restoring device of aspects 2-4, 26-35, and 44-51, wherein the stent has no openings through a stent wall.

Aspect 86. The lung elasticity restoring device of aspects 2-4, 26-35, and 44-51, wherein the stent has different configurations in the expanded state and in a delivery state.

Aspect 87. The lung elasticity restoring device of aspects 2-4, 26-29, 31-33, 35, 44-48, and 50-51, wherein the stent has the same configuration in the expanded state and in a delivery state.

Aspect 88. The lung elasticity restoring device of aspects 1-87, further comprising a respiration assistance member.

Aspect 89. The lung elasticity restoring device of aspect 88, wherein the respiration assistance member defines a single lumen.

Aspect 90. The lung elasticity restoring device of aspect 88, wherein the respiration assistance member defines a plurality of lumens.

Aspect 91. The lung elasticity restoring device of aspect 88-90, wherein the respiration assistance member is a separate member from the connecting member.

Aspect 92. The lung elasticity restoring device of aspect 91, wherein a distal end of the respiration assistance member is connected to a proximal end of a proximal fixation member.

Aspect 93. The lung elasticity restoring device of aspects 88-90, wherein the respiration assistance member is a part of the connecting member.

Aspect 94. The lung elasticity restoring device of aspects 88-93, wherein the respiration assistance member is in communication with an external device.

Aspect 95. The lung elasticity restoring device of aspect 94, wherein the external device is an external oxygen supply, a nebulizer, or a breathing assistance device.

Aspect 96. The lung elasticity restoring device of aspects 94-95, the plurality of lumens including a lumen for inflation/deflation of a balloon fixation member and a lumen in communication with the external device.

Aspect 97. The lung elasticity restoring device of aspects 88-96, wherein the respiration assistance member is connected to a tracheostomy tube, a tracheal button, or a nasal cannula.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A lung device configured to be deployed in an airway, the lung device comprising:
    a first radially expandable fixation member having a first profile in an expanded state and defining a lumen;
    a second radially expandable fixation member having a second profile in an expanded state and defining a lumen; and
    a connecting member including only one band, only one cord, or only one wire, the connecting member extending between and connecting the first radially expandable fixation member and the second radially expandable fixation member, wherein the first radially expandable fixation member and the second radially expandable fixation member are connected by only the only one band, the only one cord, or the only one wire when positioned outside of a body;
    the lung device being reversibly extendable between an inspiration configuration and an expiration configuration, the lung device being extendable to the inspiration configuration and biased to the expiration configuration, the lung device being biased to the expiration configuration by the connecting member,
    wherein an outer surface of one or more of the first radially expandable fixation member, the second radially expandable fixation member, and the connecting member, includes a bronchodilator.

2. The lung device of claim 1, wherein the first and second radially expandable fixation members are balloons.

3. The lung device of claim 1, further comprising a third radially expandable fixation member having a third profile in an expanded state.

4. The lung device of claim 1, wherein the expanded state of the first radially expandable fixation member has a greater diameter than the expanded state of the second radially expandable fixation member.

5. The lung device of claim 2, wherein the first radially expandable fixation member and the second radially expandable fixation member each includes protrusions extending at an oblique angle from an outer surface, the protrusions configured to protrude away from the alveoli when the lung device is implanted, the protrusions configured to anchor the first radially expandable fixation member and the second radially expandable fixation member in the airway.

6. The lung device of claim 1, wherein the second radially expandable fixation member has a first position relative to the first radially expandable fixation member when the lung device is in the inspiration configuration; and the second radially expandable fixation member has a second position relative to the first radially expandable fixation member when the lung device is in the expiration configuration, the second position of the second radially expandable fixation member being different than the first position.

7. A lung device comprising:
    a first expandable member having a first profile in an expanded state, the first expandable member forming a first end of the lung device;
    a second expandable member having a second profile in an expanded state, the second expandable member forming a second end of the lung device; and
    a connecting member extending between and connecting the first and second expandable members, wherein the connecting member is a tubular member having at least two lumens that extend from a proximal end to a distal end of the tubular member;
    the lung device being reversibly extendable between an inspiration state and an expiration state, the lung device being extendable to the inspiration state and biased to the expiration state by the connecting member,
    wherein an outer surface of one or more of the first expandable member, the second expandable member, and the connecting member, includes a bronchodilator.

8. The lung device of claim 7, wherein the tubular member includes exactly three lumens extending from the proximal end to the distal end of the tubular member, and further defines at least three side holes extending through a wall of the tubular member.

9. The lung device of claim 1, wherein the outer surface of one or more of the first radially expandable fixation member, the second radially expandable fixation member, and the connecting member, includes a steroid.

10. The lung device of claim 9, wherein the bronchodilator includes one or more of albuterol, levalbuteral, ipratropium tiotropium, salmeterol, formoterol, arformoterol, indacaterol, aclidinium, glycopyrronium, and darotropium, and the steroid includes one or more of bluticasone and budesonide.

11. The lung device of claim 1, wherein one or more of the first radially expandable fixation member, the second radially expandable fixation member, and the connecting member includes a biodegradable material.

12. The lung device of claim 11, wherein each of the first radially expandable fixation member, the second radially expandable fixation member, and the connecting member includes a biodegradable material.

13. The lung device of claim 12, wherein the biodegradable material includes one or more of polylactic acid, polyglycolic acid (PGA), collagen, polycaprolactone, and hyaluronic acid.

14. The lung device of claim 1, further including a valve configured to move between a fully-open state when the lung device is in the inspiration configuration and a partially-closed state when the lung device is in the expiration configuration, wherein the valve includes one or more flaps configured to extend substantially parallel to a longitudinal axis of the lung device in the fully-open state, and extend radially inward from an inner wall of the valve in the partially-closed state.

15. A lung device comprising:
a first balloon having a first profile in an expanded state, the first balloon forming a first end of the lung device;
a second balloon having a second profile in an expanded state, the second expandable member forming a second end of the lung device; and
a connecting member extending between and connecting the first and second balloons, wherein the first balloon and the second balloon are connected by only the connecting member when the lung device is positioned outside of a body, and the connecting member is a tubular member defining at least two lumens that extend from a proximal end to a distal end of the tubular member;
the lung device being reversibly extendable between an inspiration state and an expiration state, the lung device being extendable to the inspiration state and biased to the expiration state by the connecting member,
wherein an outer surface of each of the first balloon, the second balloon, and the connecting member, includes a bronchodilator and a steroid, the bronchodilator includes one or more of albuterol, levalbuteral, ipratropium tiotropium, salmeterol, formoterol, arformoterol, indacaterol, aclidinium, glycopyrronium, and darotropium, and the steroid includes one or more of bluticasone and budesonide.

16. The lung device of claim 15, wherein each of the first balloon, the second balloon, and the connecting member includes a biodegradable material including one or more of polylactic acid, polyglycolic acid (PGA), collagen, polycaprolactone, and hyaluronic acid.

17. The lung device of claim 16, further including a valve configured to move between a fully-open state when the lung device is in the inspiration state and a partially-closed state when the lung device is in the expiration state, wherein the valve includes one or more flaps configured to extend substantially parallel to a longitudinal axis of the lung device in the fully-open state, and extend radially inward from an inner wall of the valve in the partially-closed state.

* * * * *